(12) United States Patent
Adam et al.

(10) Patent No.: US 7,025,724 B2
(45) Date of Patent: *Apr. 11, 2006

(54) WAVELET DEPULSING OF ULTRASOUND ECHO SEQUENCES

(75) Inventors: Dan Adam, Haifa (IL); Oleg Michailovich, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 495 days.

This patent is subject to a terminal disclaimer.

(21) Appl. No.: 10/275,806

(22) PCT Filed: Apr. 27, 2001

(86) PCT No.: PCT/US01/13590

§ 371 (c)(1),
(2), (4) Date: Jan. 29, 2003

(87) PCT Pub. No.: WO01/85011

PCT Pub. Date: Nov. 15, 2001

(65) Prior Publication Data

US 2004/0054281 A1 Mar. 18, 2004

Related U.S. Application Data

(60) Provisional application No. 60/203,510, filed on May 11, 2000.

(51) Int. Cl.
*A61B 8/00* (2006.01)

(52) U.S. Cl. .................................................. 600/437

(58) Field of Classification Search ......... 600/437–472; 73/602, 625, 626; 342/145
See application file for complete search history.

(56) References Cited

U.S. PATENT DOCUMENTS

| | | | | | |
|---|---|---|---|---|---|
| 4,063,549 | A | * | 12/1977 | Beretsky et al. | 600/443 |
| 5,760,732 | A | * | 6/1998 | Marmarelis et al. | 342/145 |
| 5,943,006 | A | * | 8/1999 | Crane et al. | 342/196 |
| 6,443,895 | B1 | * | 9/2002 | Adam et al. | 600/443 |

OTHER PUBLICATIONS

A. K. Louis, "Approximative inverse for linear and some nonlinear problems", Inverse Problems, vol. 11 No. 6 pp. 1211–1223 (1995).

E. Sekko, G. Thomas, A. Boukrouche, "A deconvolution technique using optimal Wiener filtering and regularization", Signal processing, 72, pp. 23–32, 1999.

Torfinn Taxt, "Comparison of cepstrum–based methods for radial blind deconvolution of ultrasound images", IEEE Transatcions on Ultrasonics, Ferroelectrics and Frequency Control, vol. 44, No. 3, May 1997.

(Continued)

*Primary Examiner*—Ali Imam
(74) *Attorney, Agent, or Firm*—Mark M. Friedman

(57) ABSTRACT

Methods and associated apparatuses for imaging a target. An echo sequence image of the target is acquired and a log spectrum of at least a portion of the echo sequence image is computed. A point spread function is estimated by one of two methods. According to the first method, a low-resolution wavelet projection of the echo sequence log spectrum is used as an estimate of the log spectrum of the point spread function. According to the second method, an outlier-resistant wavelet transform of the echo sequence log spectrum is effected, followed by soft-thresholding and an inverse wavelet transform. Under both methods, a frequency domain phase of the point spread function also is estimated, the relevant portion of the echo sequence image is deconvolved using the estimated point spread function.

22 Claims, 4 Drawing Sheets

OTHER PUBLICATIONS

Torfinn Taxt, "Restoration of medical ultrasound images using two-dimensional homomorphic deconvolution", IEEE Transactions on Ultrasonics, Ferroelectrics and Frequency Control, vol. 42, No. 4, Jul. 1995.

J. A. Jensen and S. Leeman, "Nonparametric estimation of ultrasound pulses", IEEE Transactions on Biomedical Engineering, vol. 41, pp. 929–936, 1994.

Kjetil F. Kaaresen and Erik Bolviken, "Blind deconvolution of ultrasonic traces accounting for pulse variance"; IEEE Transactions on Ultrasonics, Ferroelectrics and Frequency Control, vol. 46, NO. 3, May 1999.

Udantha R. Abeyratne, Athina P. Petropulu, John M. Reid, "Higher order spectra based deconvolution of ultrasound images", IEEE Transactions on Ultrasonics, Ferroelectrics amd Frequency Control, vol. 42, NO. 6, Nov. 1995.

J. A. Jensen, "Deconvolution of ultrasound images", Ultrasonic Imaging, vol. 14 pp. 1–15 (1992).

"Simultaneous speckle reduction and data compression using best wavelet packet bases with application to SAR based ATD/R", D. Wei, J. E. Odegard, M. Lang, and C. S. Burrus, SPIE, vol. 2491, 1995.

"Speckle reduction via Wavelet Shrinkage with application to SAR based ATD/R", H. Guo, J. E. Odegard, M. Lang, R. A. Gopinath, I. W. Selesnick, and C. S. Burrus, SPIE, vol. 2303, 1994.

David L. Donoho and Ronald R. Coifman, "Translation-invariant de-noising", Technical Report 475, Department of Statistics, Stanford University, (May 1995).

"De-noising and robust non-linear Wavelet analysis", Andrew G. Bruce, David L. Donoho, Hong-Ye Gao, R. Douglas Martin, SPIE, vol. 2242, 1994.

"Ideal De-noising in an Orthonormal Basis Chosen from a Library of Bases", David L. Donoho and Iain Johnstone, 1994.

"De-noising by Soft-Thresholding", David L. Donoho, 1992.

"Adapting to Unknown Smoothness via Wavelet Shrinkage "David L. Donoho and Iain Johnstone, 1993.

"Wavelet shrinkage and Wavelet Vaguelette Decomposition: A Ten-Minute Tour", David L. Donoho, 1993.

"Nonlinear processing of a shift invariant DWT for noise reduction", M. Lang, H. Guo, J. E. Odegard, and C. S. Burrus, SPIE, vol. 2491, 1995.

D. G. Childers, D. P. Skinner and R. C. Kemmerait, "The cepstrum: A guide to processing", Processing IEEE, vol. 65, pp. 1428–1443, 1977.

"Properties of speckle integrated with a finite aperture and logarithmically transformed", H. H. Arsenault, G. Apr., Journal of Optical Society of America, 66, Nov., 1976.

* cited by examiner

WAVELET DEPULSING OF ULTRASOUND ECHO SEQUENCES

REFERENCE TO PRIORITY APPLICATION

This application is a national stage application of PCT/US01/13590 filed Apr. 27, 2001. This application also claims priority to U.S. Provisional Application No. 60/203,510 filed May 11, 2000.

FIELD AND BACKGROUND OF THE INVENTION

The present invention relates to medical imaging and, more particularly, to a method of deconvolving an ultrasonic echo sequence, and to an ultrasound imaging apparatus that employs this method.

Because of the coherence of the back-scattered echo signals, images obtained from echo ultrasound imaging systems have extremely complex patterns that bear no obvious relationship to the macroscopic properties of the insonified object. The vast majority of biological tissues are extremely small on the scale of an acoustic wavelength. Consequently, a signal obtained within a resolution cell consists of contributions of many independent scatterers. Interference of these de-phased echoes gives rise to a pattern that has the appearance of a chaotic jumble of "speckles", known as speckle noise. The speckle pattern consists of a multitude of bright spots where the interference is highly constructive, dark spots where the interference is destructive, and brightness levels between these extremes. The presence of speckle noise in an ultrasound image reduces the ability of a user to resolve fine details. Speckle noise obscures very small structures, for example, early stage tumors, and decreases the reliability of tissue characterization. Therefore, the suppression of speckle noise is an important component of medical ultrasound imaging.

For the purpose of modeling the interaction of biological tissue with ultrasonic waves, the biological tissue is considered to be an assembly of reflectors and scatterers. A reflector is a plane interface that is large compared to the wavelength and that reflects portions of the transmitted energy back towards the transmitter. A scatterer is an object that is small compared to the wavelength and that scatters the transmitted signal in all directions. Such a system often is modeled as a (most generally 3D) function called the spatial response of insonified material, the reflectivity function, or (in medical applications) the spatial tissue response.

An ultrasound radio frequency (RF) image can be considered to consist of 1D echo sequences, also known as "RF lines". Assuming the tissue properties to be uniform in the plane perpendicular to the scanning beam, an acquired 2D RF image can be viewed as the result of the convolution of the 2D reflectivity function (which accounts for inhomogeneity in the scanning plane) and the 2D transducer point spread function (PSF). Thus, the RF image can be considered to be a distorted version of the true reflectivity function, where the distorting kernel is the transducer PSF. This distortion includes the speckle noise discussed above.

In principle, it should be possible to measure the PSF in a calibration procedure, and then to deconvolve the PSF from the RF image. In practice, however, this is not possible, for several reasons. Perhaps the most important reason is that the absorption of ultrasound energy in tissues increases with frequency. This frequency-dependent attenuation causes both the PSF amplitude and the PSF shape to depend on depth in the tissue, leading to the observed non-stationarity of RF sequences.

In medical ultrasound, a pulse is transmitted into the tissue to be imaged, and the echoes that are backscattered to the emitting transducer are detected as a voltage trace RF line. The RF line conventionally is modeled as being a convolution of a hypothetical 1D PSF with a hypothetical 1D tissue reflectivity function. Assuming that the scatterers on each image line are located on a uniform grid and that the system impulse response is range shift invariant along each image line, a discretized version of the received signal can be written as:

$$rf[n]=a[n]*s[n]+\text{noise}[n] \quad (1)$$

where n is a time index, rf[n] is the RF line, s[n] is the transmitted ultrasound PSF, a[n] is a reflectivity sequence corresponding to the reflectivity function, noise[n] is measurement noise, and "*" represents convolution. Because the frequency-dependent attenuation process appears as a decrease with distance of the mean frequency and amplitude of the PSF, it is commonly assumed that the received echo signal may be expressed as a depth-dependent PSF convolved with the tissue reflectivity function. To make the PSF "location dependent", s[n] in equation (1) is replaced by s[n,k], where k is the location index. This leads to the observed non-stationarity of the RF lines received from the tissue. In order to deal with this non-stationarity, the RF-sequence is broken up into a number of possibly overlapping segments, such that within each segment the frequency-dependent attenuation process can be ignored and equation (1) holds. The problem of tissue characterization is thus reduced to a set of blind deconvolution problems: for each segment of a given RF line, the respective ultrasonic PSF should be estimated and removed.

To this end, homomorphic signal processing has been applied to rf[n]. Ignoring the noise term on the right hand side of equation (1) for now, transforming equation (1) to the frequency domain gives:

$$RF(w)=A(w)S(w) \quad (2)$$

i.e., in the frequency domain, the frequency spectrum A(w) of the reflectivity sequence is multiplied by the frequency spectrum S(w) of the PSF to give the frequency spectrum RF(w) of the echo sequence. These spectra can be written as $$RF(w)=|RF(w)|e^{j \cdot \arg(RF(w))} \quad (3)$$

$$A(w)=|A(w)|e^{j \cdot \arg(A(w))} \quad (4)$$

$$S(w)=|S(w)|e^{j \cdot \arg(S(w))} \quad (5)$$

Taking the complex logarithm of both sides of equation (2) then gives $$\log|RF(w)|=\log|A(w)|+\log|S(w)| \quad (6)$$

$$\arg[RF(w)]=\arg[A(w)]+\arg[S(w)] \quad (7)$$

As described in the Annexes, the log spectrum of the echo sequence, log|RF(w)|, thus is a sum of a smooth and regular log spectrum, log|S(w)|, of the PSF and a jagged and irregular log spectrum, log|A(w)|, of the reflectivity sequence. Cepstrum-based techniques have been used to exploit the qualitatively different natures of the PSF and reflectivity log spectra to isolate the PSF log spectrum for the purpose of estimating the PSF and deconvolving the estimated PSF from the echo sequence. See, for example, Torfinn Taxt, "Restoration of medical ultrasound images using two-dimensional homomorphic deconvolution", *IEEE Transactions on Ultrasonics, Ferroelectrics and Frequency*

*Control*, vol. 42 no. 4 pp. 543–554 (July 1995); Torfinn Taxt, "Comparison of cepstrum-based methods for radial blind deconvolution of ultrasound images", *IEEE Transactions on Ultrasonics, Ferroelectrics and Frequency Control*, vol. 44 no. 3 pp. 666–674 (May 1997); J. A. Jensen and S. Leeman, "Nonparametric estimation of ultrasound pulses", *IEEE Transactions on Biomedical Engineering*, vol. 41 pp. 929–936 (1994); and J. A. Jensen, "Deconvolution of ultrasound images", *Ultrasonic Imaging*, vol. 14 pp. 1–15 (1992). Cepstrum-based techniques, however, suffer from certain limitations, as discussed in Annex A. Briefly, the complex cepstrum of a signal of finite duration has been shown to extend to infinity. This invariably leads to aliasing errors when the Discrete Fourier Transform or a similar discrete numerical method is used to compute the cepstrum.

There is thus a widely recognized need for, and it would be highly advantageous to have, a method of estimating an ultrasound PSF that would overcome the disadvantages of presently known methods as described above.

SUMMARY OF THE INVENTION

The present invention includes two innovative methods for estimating the PSF of an echo sequence. The first method is based on a low-resolution wavelet projection of the log spectrum of the echo sequence. The second method is based on the "soft-thresholding de-noising" algorithm of David L. Donaho and his coworkers, modified to account for the fact that the log spectrum of the reflectivity sequence is not normally distributed.

According to the present invention there is provided a method of imaging a target, including the steps of: (a) acquiring an echo sequence image of the target; (b) computing a log spectrum of at least a portion of the echo sequence image; (c) computing a low-resolution wavelet projection of the log spectrum; (d) estimating a point spread function from the low-resolution wavelet projection; and (e) deconvolving the at least portion of the echo sequence image with the point spread function.

According to the present invention there is provided a method of imaging a target, including the steps of: (a) acquiring an echo sequence image of the target; (b) computing a log spectrum of at least a portion of the echo sequence image; (c) effecting an outlier-resistant wavelet transform of the log spectrum, thereby producing a plurality of wavelet coefficients; (d) soft-thresholding the wavelet coefficients; (e) applying an inverse wavelet transform to the soft-thresholded wavelet coefficients to obtain a point spread function log spectrum; (f) estimating a point spread function from the point spread function log spectrum; and (g) deconvolving the at least portion of the echo sequence image with the point spread function.

According to the present invention there is provided an apparatus for imaging a target, including: (a) a transducer for acquiring an echo sequence image of the target; and (b) a processor for: (i) computing a log spectrum of at least a portion of the echo sequence image, (ii) computing a low-resolution wavelet projection of the log spectrum, (iii) estimating a point spread function from the low-resolution wavelet projection, and (iv) deconvolving the at least portion of the echo sequence image with the point spread function.

According to the present invention there is provided an apparatus for imaging a target, including: (a) a transducer for acquiring an echo sequence image of the target; and (b) a processor for: (i) computing a log spectrum of at least a portion of the echo sequence image, (ii) effecting an outlier-resistant wavelet transform of the at least portion of the log spectrum, thereby producing a plurality of wavelet coefficients, (iii) soft-thresholding the wavelet coefficients, (iv) applying an inverse wavelet transform to the soft-thresholded wavelet coefficients to obtain a point spread function log spectrum, (v) estimating a point spread function from the point spread function log spectrum, and (vi) deconvolving the at least portion of the echo sequence image with the point spread function.

According to both methods of the present invention, an echo sequence image of the target is acquired. As understood herein, an echo sequence image is a set of RF lines, acquired in parallel, from which the final video image of the target is to be calculated. Optionally, the echo sequence image is partitioned into a plurality of segments that may be either disjoint or overlapping. Subsequent processing is applied either to the echo sequence image as a whole or to one or more of the segments separately. This processing begins with the computation of the log spectrum of the time series (the whole echo sequence or the segment thereof) being processed.

At this point, the two methods of the present invention diverge temporarily. According to the first method, a low-resolution wavelet projection of the log spectrum is computed. Preferably, this wavelet projection is based on a Coiflet wavelet, on a minimum-phase Daubechies wavelet, on a symmetric Daubechies wavelet or on a biorthogonal wavelet. Optionally, this wavelet projection includes an outlier-resistant wavelet transform of the log spectrum.

According to the second method, an outlier-resistant wavelet transform is essential, not merely optional. Specifically, according to the second method, an outlier-resistant wavelet transform of the log spectrum is effected, and the resulting wavelet coefficients are subjected to the "soft-thresholding" algorithm of David L. Donaho et al., or an equivalent algorithm. The outlier-resistant wavelet transform preferably is based on minimizing an $L_1$ norm. Most preferably, the outlier-resistant wavelet transform is the Smoother-Cleaner Wavelet Transform of Andrew G. Bruce et al., or an equivalent transform. Robust residuals may be removed at all resolution levels of the outlier-resistant wavelet transform or at only some resolution levels. In particular, robust residuals may be removed at only the first resolution level. An inverse wavelet transform is applied to the soft-thresholded wavelet coefficients, thereby producing a PSF log spectrum.

Either the low-resolution wavelet projection of the first method or the PSF log spectrum of the second method is an estimate of $\log|S(w)|$. The remaining steps of the two methods are identical. An estimate of the frequency domain phase $\arg[S(w)]$ of the PSF is obtained, preferably under the assumption that the PSF is a minimum phase sequence. Optionally, a Wiener filter is applied to the estimate of $|S(w)|$. Equation (5) now gives an estimate of $S(w)$, which is inverse Fourier transformed to give an estimate of the PSF. Finally, the estimated PSF is deconvolved from the time series (the whole echo sequence or the segment thereof) being processed preferably using an approximate inverse.

An apparatus of the present invention includes a transducer for acquiring an echo sequence image of the target and a processor for processing the acquired echo sequence image according to one of the two methods.

Although the present invention is illustrated herein with reference to its primary application to ultrasound imaging, it is to be understood that the scope of the present invention extends to any imaging modality based on receiving echoes of signals transmitted by an impulsive energy source to a target, and to which the principles of the present invention are germane (for example, seismic exploration).

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of methods, and associated systems, for acquiring an echo sequence image of a target using an impulsive source of energy, and then estimating and deconvolving the point spread function of the impulsive source. Specifically, the present invention can be used to acquire medical ultrasound images with reduced speckle noise.

The principles and operation of echo sequence image acquisition and processing according to the present invention may be better understood with reference to the drawings and the accompanying description.

Figure 1:
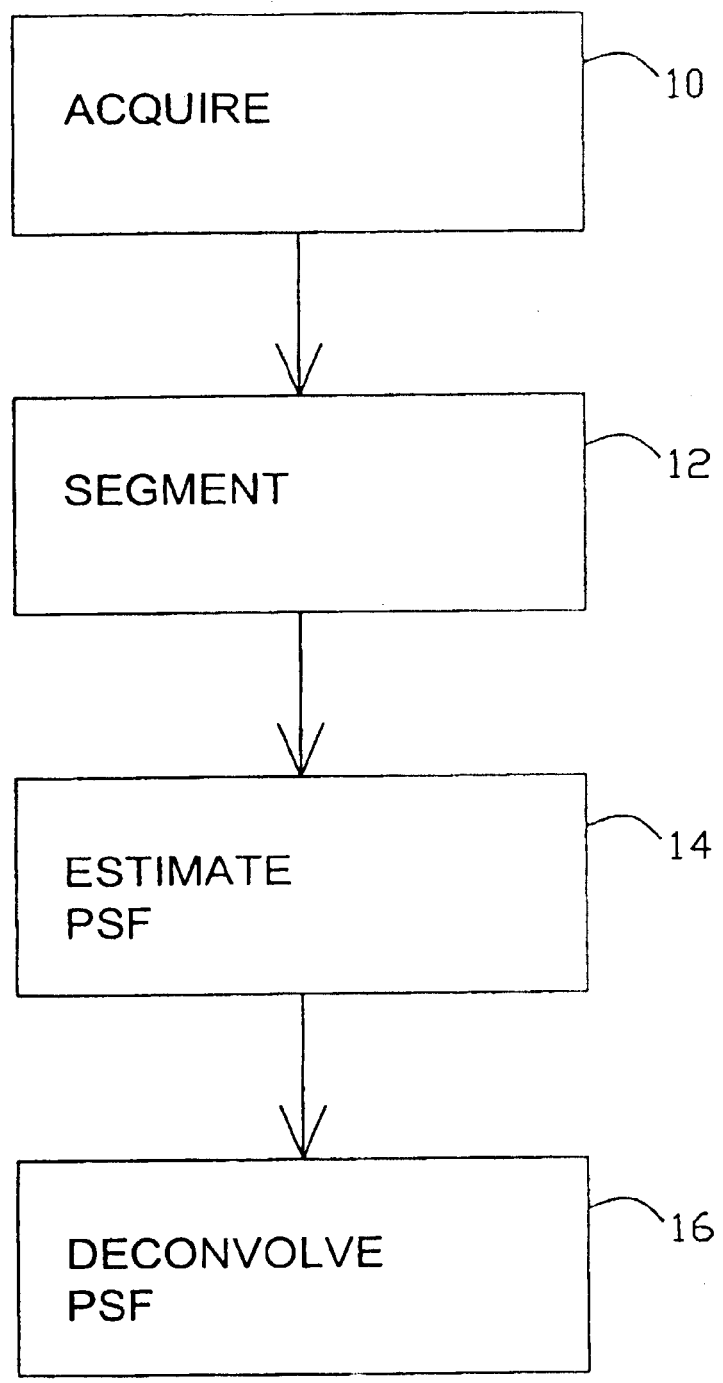
FIG. 1 is an overall flowchart of the methods of the present invention.

Referring now to the drawings, FIG. 1 is an overall flowchart of the methods of the present invention.

In block 10, a 1D ultrasound echo sequence is acquired in the conventional manner.

In block 12, the acquired echo sequence is optionally partitioned into two or more subsequences. As described in Annex A with reference to equation (2.1) (and with a slight change in notation), biological tissue acts as a low pass acoustic filter, so that the frequency content of an ultrasound pulse decreases with time. To compensate for this effect, the echo sequence rf[n] usually is partitioned into a set of subsequences rf[n,k], such that, in each subsequence, the ultrasound PSF s[n,k] can be considered to have a well-defined frequency spectrum. The subsequences rf[n,k] may be either disjoint (i.e., nonoverlapping), or may overlap to a certain extent. In what follows, the subsequence index k will be suppressed for notational clarity.

In block 14, the PSF is estimated. The present invention includes two methods of estimating the PSF. More precisely, the present invention includes two methods of estimating log|S(w)|. According to the first method, which is described in detail in Annex A, a low-resolution wavelet projection of log|RF(w)| is taken to represent log|S(w)|. According to the second method, which is described in detail in Annex B, log|RF(w)| is treated as a noisy representation of log|S(w)|, and the noise is removed using the "soft-thresholding de-noising" algorithm of David L. Donaho and his coworkers, modified to account for the fact that the samples of log|A(w)| are not distributed according to a normal (Gaussian) distribution. Under either method, arg[S(w)] is estimated as described below. Equation (5) then gives an estimate of S(w), whose inverse Fourier transform is the PSF.

In block 16, the estimated PSF is deconvolved from the echo sequence to give an estimate of the reflectivity sequence, as described below.

Figure 2:
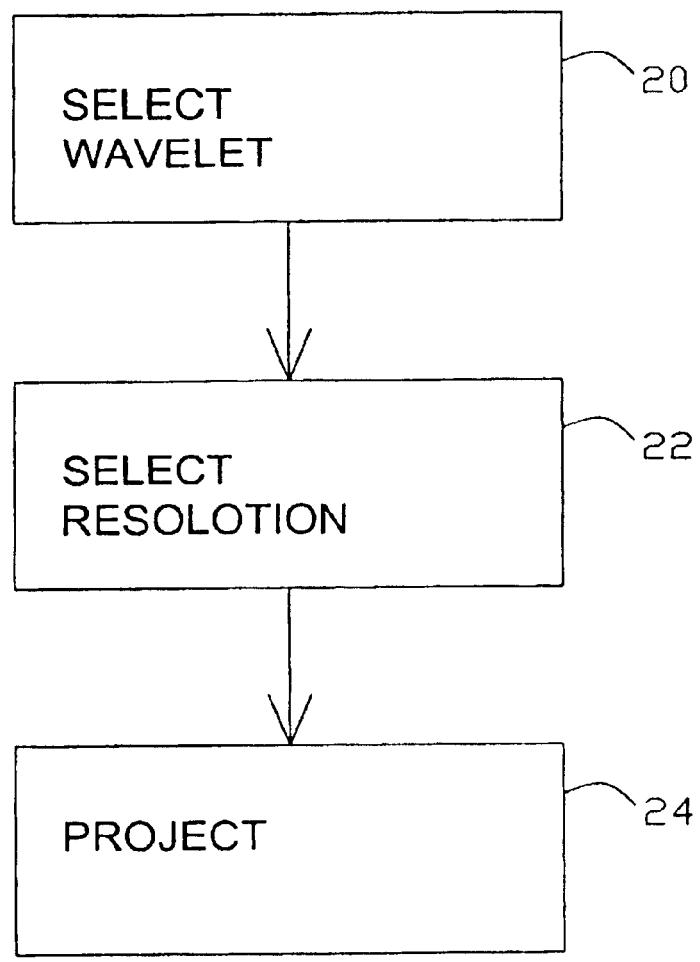
FIG. 2 is a flowchart of the low-resolution wavelet projection procedure.

FIG. 2 is a flowchart of the low-resolution wavelet projection procedure.

In block 20, the wavelet used in the wavelet decomposition of log|RF(w)| is selected. Suitable wavelets include, among others, Coiflet wavelets, minimum-phase Daubechies wavelets, symmetric Daubechies wavelets and biorthogonal wavelets, with Coiflet wavelets being preferred.

In block 22, the resolution level of the wavelet transform that distinguishes log|A(w)| from log|S(w)| is selected. One way of doing this is to calibrate the ultrasound probe by recording the pulse emitted by the probe, either directly or after reflection from a single planar reflector, treating this recorded pulse as a proxy for s[n], computing the corresponding log|S(w)| and determining the number of wavelet coefficients needed to represent this proxy for log|S(w)| with the desired degree of accuracy. As mentioned above, this measured proxy for s[n] can not be used directly for deconvolution of an acquired ultrasound echo sequence, for several reasons. First, the actual s[n] generally is low-pass filtered by the biological tissue. Second, the actual s[n] always differs from the proxy s[n] because of invariable variations in the conditions of acquisition, such as the degree of acoustical impedance mismatch between the ultrasound probe and the target. Nevertheless, the proxy of log|S(w)| can be used to define the resolution level of the wavelet transform because the wavelet resolution levels needed to accurately represent the actual log|S(w)| and the proxy of log|S(w)| generally are identical.

The low-resolution wavelet projection itself is defined in equation (3.10) of Annex A. With a slight change of notation, this equation is:

$$\log|RF(w)| = A_{2^J} \log|RF(w)| + \sum_{j \leq J} D_{2^j} \log|RF(w)| \quad (8)$$

Note that resolution level decreases with increasing resolution index j. The first term on the right hand side of equation (8), $A_{2^J} \log|RF(w)|$, is the low-resolution wavelet projection of log|RF(w)| at resolution level J that is computed in block 24. The remainder of the right hand side of equation (8) is the high-resolution portion of log|RF(w)|. $A_{2^J} \log|RF(w)|$ is used in subsequent processing as an estimate of log|S(w)|.

The second method of estimating log|S(w)| is an extension of the "soft thresholding de-noising" algorithm that was developed by David L. Donaho and his coworkers, and that they have described in a series of publications: David L. Donaho, "De-noising by soft-thresholding", *Transactions on Information Theory*, vol. 41 no. 3 pp. 613–627 (1995); David L. Donaho and Iain M. Johnstone, "Adapting to unknown smoothness via wavelet shrinkage", *Journal of the American Statistical Association*, vol. 90 pp. 1200–1224, (1993); David L. Donaho and Iain M. Johnstone, "Ideal de-noising in an orthonormal basis chosen from a library of bases", *C. R. Acad. Sci. Paris, Series I*, vol. 319 pp. 1317–1322 (1994); and David L. Donaho and Ronald R. Coifman, "Translation-invariant de-noising", Technical Report 475, Department of Statistics, Stanford University, (May 1995). This algorithm, and equivalent algorithms, are referred to herein collectively as "soft-thresholding" algorithms. The purpose of these algorithms is to clean up the noise of a noisy signal in order to extract the signal. In the present context, log|S(w)| is treated as the signal part of log|RF(w)| and log|A(w)| is treated as the noise part of log|RF(w)|: these algorithms are applied to log|RF(w)| to clean up log|A(w)|, thereby isolating and extracting log|S (w)|. These algorithms assume that the noise obeys a Gaussian distribution. It is shown in Annex B that $\log|A(w)|$, treated as random noise, is expected to obey a non-Gaussian distribution, specifically, a Fisher-Tippet distribution. To account for this, the wavelet coefficients of $\log|RF(w)|$, that are input to the soft-thresholding algorithm, are computed using an outlier-resistant wavelet transform. Essentially, wavelet projections are used that minimize the $L_1$ norm instead-of the $L_2$ norm at each level of resolution. In practice, for computational efficiency, the "Smoother-Cleaner Wavelet Transform" (Andrew G. Bruce, David L. Donoho, Hong-Ye Gao and R. Douglas Martin, SPIE Vol. 2242 pp. 325–336 (1994)) is used in preference to brute force $L_1$-norm minimization.

Figure 3:
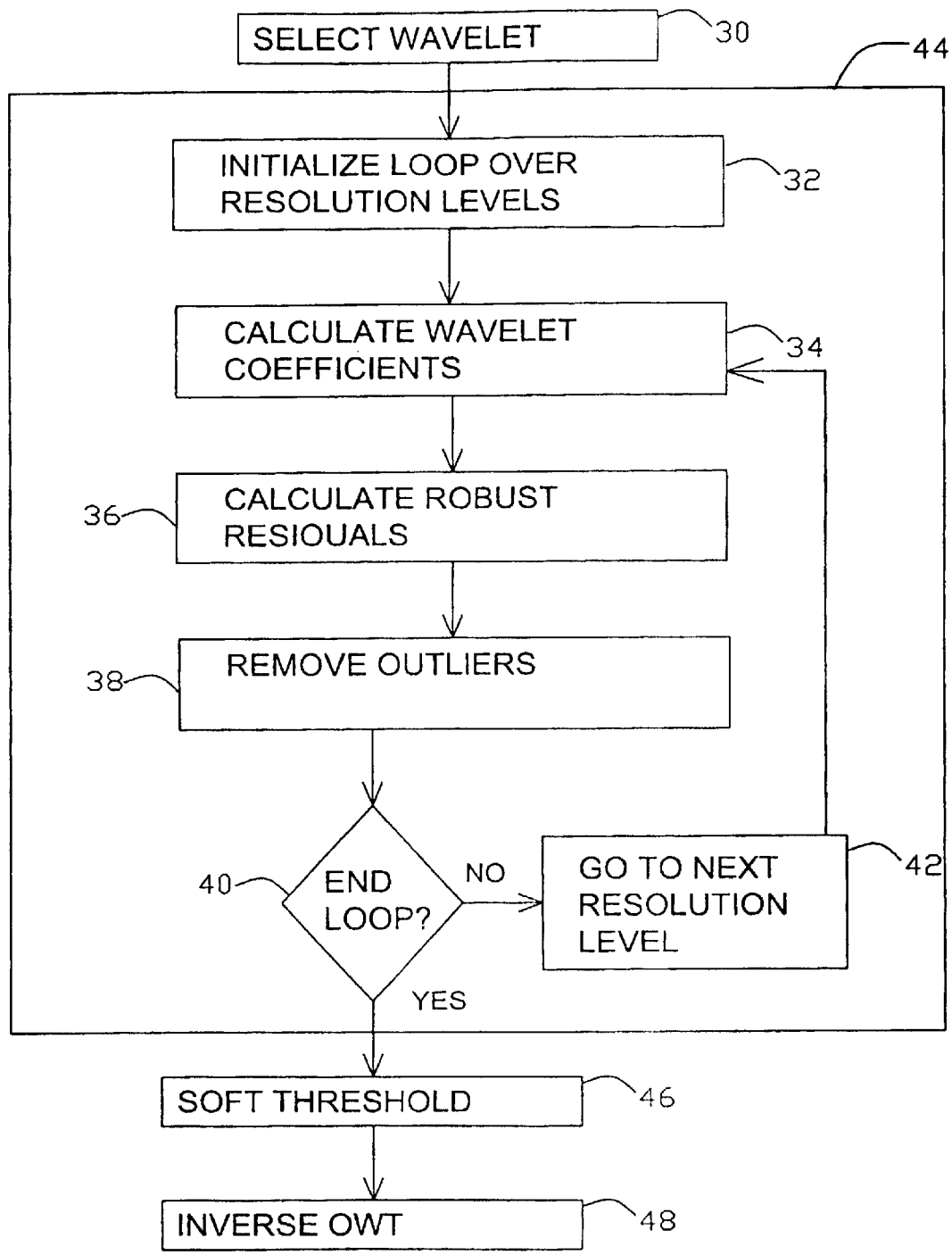
FIG. 3 is a flowchart of the second method of estimating log|S(w)|.

FIG. 3 is a flowchart of the second method of estimating $\log|S(w)|$.

As in the low-resolution wavelet projection of FIG. 2, the first step (block 30) is the selection used in the discrete wavelet transform of $\log|RF(w)|$. The outlier-resistant discrete wavelet transform itself is effected in block 44, as a loop over resolution levels. The loop is initialized in block 32 at the coarsest resolution level. At each resolution level, wavelet coefficients are calculated in block 34, robust residuals are calculated in block 36, and the thus-identified outliers are removed in block 38. In block 40, the loop termination condition is tested: if the finest desired resolution has not been reached, the resolution level is made finer (block 42) and the loop is repeated; otherwise the loop is terminated.

As discussed above and in Annex B, the robust residual calculation of block 36 amounts to computing the wavelet coefficients by minimizing an $L_1$ instead of an $L_2$ norm at each level of resolution. This minimization can be done by brute force. It is preferable, however, for numerical efficiency, to use the "Smoother-Cleaner Wavelet Transform" of Bruce et al. for this purpose.

Following the outlier-resistant wavelet transform of block 44, the soft thresholding algorithm of Donaho and his coworkers is applied to the resulting wavelet coefficients in block 46, and the soft-thresholded wavelet coefficients are subjected to an inverse discrete wavelet transform in block 48 to give the final estimate of $\log|S(w)|$.

Although FIG. 3 shows robust residuals being calculated and outliers being removed at all the resolution levels considered, it has been found that it is not strictly necessary to remove outliers at all resolution levels. In fact, it often suffices to remove outliers only at the first (coarsest) resolution level.

It will be appreciated that the outlier resistant wavelet transform of block 44 also may be used in the low-resolution wavelet projection procedure of FIG. 2, in the projection step of block 24.

Optionally, following the exponentiation of the estimate of $\log|S(w)|$ obtained by either method, the Wiener filter defined by equation (3.11) of Annex A is used to refine this exponentiated estimate to provide a refined estimate of $|S(w)|$.

$|S(w)|$ having been estimated, $\arg[S(w)]$ now is estimated. As described in Annex A, the preferred estimate of $\arg[S(w)]$ is a minimum phase estimate. If it is assumed that the PSF is a minimum phase sequence, then $\log|S(w)|$ and $\arg[S(w)]$ are a Hilbert transform pair, so that an estimate of $\arg[S(w)]$ can be derived from the estimate of $\log|S(w)|$.

With both $|S(w)|$ and $\arg[S(w)]$ now estimated, equation (5) gives an estimate of $S(w)$. The inverse Fourier transform of this estimate of $S(w)$ is an estimate of $s[n]$, which is deconvolved from $rf[n]$ by approximate inverse methods, as described, for example, in A. K. Louis, "Approximative inverse for linear and some nonlinear problems", *Inverse Problems*, vol. 11 no. 6 pp. 1211–1223 (1995).

Figure 4:
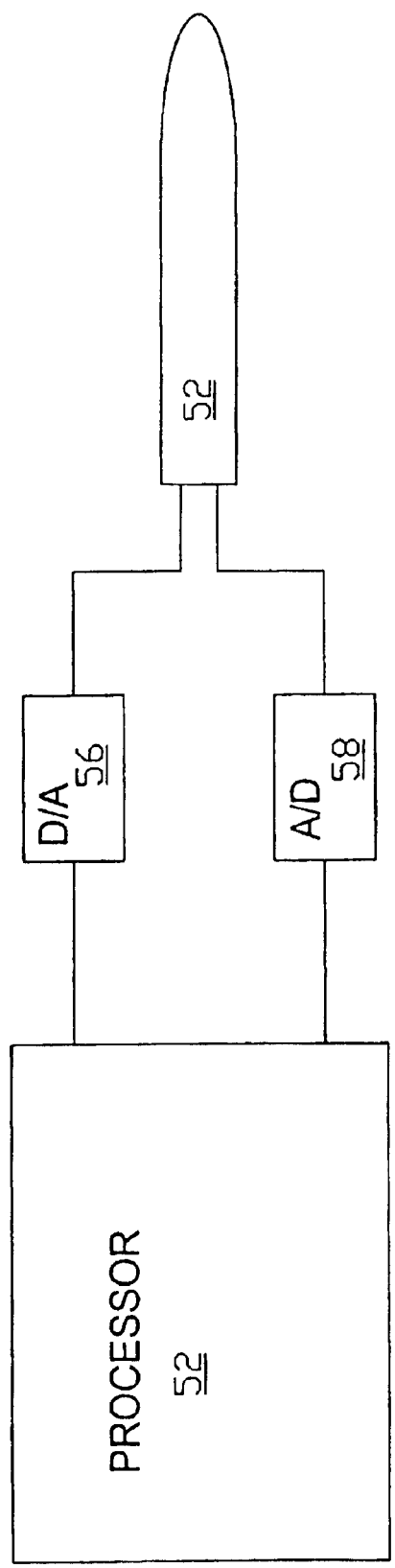
FIG. 4 is a high level block diagram of an ultrasound imaging apparatus of the present invention.

FIG. 4 is a high level block diagram of an ultrasound imaging apparatus 50 of the present invention. Apparatus 50 includes a conventional ultrasound transducer 52 coupled to a digital processor 54 via a D/A converter 56 and an A/D converter 58. Processor 54 generates digital ultrasound waveforms that are transformed to analog signals by D/A converter 56 and transmitted into the biological target to be imaged by transducer 52. The consequent ultrasound echoes are received by transducer 52, digitized by A/D converter 58 and processed by processor 54 in accordance with the principles of the present invention to provide images of the target with reduced speckle noise.

While the invention has been described with respect to a limited number of embodiments, it will be appreciated that many variations, modifications and other applications of the invention may be made.

ANNEX A

"Nonparametric estimation of ultrasonic pulses using the FWT and reflectivity function acquisition by the approximate inverse technique"

Dan Adam and Oleg Michailovich

1. INTRODUCTION

In order to describe scattering of the ultrasound from soft tissues several theoretical approaches exist. One way is to consider the acoustic inhomogeneity as an assembly of *reflectors* and *scatterers*. The former is a plane and large, compared to the wavelength, interface reflecting portions of the transmitted energy back toward the transmitter, and the latter is a small object, compared to the wavelength, spreading the transmitted signal in all directions, reflecting small portions of the energy. Such a system can be generally modeled as a some function supplying us for each point of interrogated tissue reflection strengths, and it is a measure of how much of the transmitted energy is reflected by an imaginary point reflector located at the given point. This function is frequently called the *spatial response of insonified material* and it strongly depends on the transmitter aperture position and geometry. Further we will refer to it as the *spatial tissue response* or *reflectivity function*. With certain assumptions, which will be discussed latter, any received *radio - frequency (RF)* image can be modeled as a convolution product of the spatial impulse response of the observed tissue and the *transducer point spread function (PSF)*. Note that both the tissue reflectivity function and the transducer PSF are generally 3-D functions, but the dimension of the problem can be decreased by several ordinary assumptions, which might be made without affecting the model preciseness.

In order to improve the transducer resolution, diverse kinds of apertures (namely, curved, phased arrays) are used. Such devices have electronic focusing in the lateral direction (transverse to the beam) and by curving the piezoelectric elements a fixed (not electronic) focus in the elevation plane also can be obtained. The ultrasound beam scanning is, usually, performed in the horizontal (transducer) plane. For such a scheme, the received RF-image $G(n,m)$ can be modeled as a 2-D convolution of the 2-D transducer PSF $S(n,m)$ and the 2-D tissue reflectivity function $F(n,m)$ [1-2, 4,6].

$$G(n,m) = S(n,m) * F(n,m) + U(n,m) \qquad (1.1)$$

Here $U(n,m)$ is the white noise taken from the normal distribution with zero-mean and variance $\sigma_u^2$ that always has to be added for real systems; the indices $n$ and $m$ are lateral and depth (axial) increments, respectively. Note that the mapping from 3-D space to 2-D space leads to non-uniqueness of solution in general. Yet if we assume that all image features in the imaging plane extend (in limits of an effective height of the beam) perpendicular to the corresponding plane in the tissue space, then the 2-D model is considered to be precise enough [1].

Thus, one can see that the RF image can be considered to be a distorted version of the true tissue reflectivity image, where the distorting kernel is the transducer PSF and, consequently, the image quality fairly depends on its spatial-frequency properties. The lateral system resolution (lateral "smearing" of the PSF) is inversely proportional to the beam width, mainly depends on the aperture geometry. In order to obtain a uniform focus width throughout the image field, *expanding apertures* are used, in which the number of the receiving elements is reduced for shallow depth and gradually increased with depth. Thus, one can assume the lateral resolution to be uniform along the image depth. The axial transducer resolution is a function of the wavelength and "time smearing" of PSF. The quality of ultrasound systems is fairly defined by these resolutions.

This paper presents an algorithm for improving the axial resolution of the imaging system by the *deconvolution* of the RF image in the axial direction. In such a case, we further simplify the above-mentioned convolution equation and model the RF-image as combined of 1-D RF-sequences. Such approach has a few drawbacks, one of which is that the high correlation of the adjacent RF-sequences is not treated, appearing as a lateral smearing of the image. Yet for some applications, the proposed modeling may be quite sufficient and fruitful.

In the given model each RF-sequence is assumed to be a convolution product of the 1-D PSF of the ultrasound transducer, $s[n]$, and the spatial tissue response taken along one direction, $f[n]2$ [5]. Further, we will refer to the 1-D transducer PSF as an *ultrasonic pulse*, meaning that if the piezoelectric element electromechanical response was a digital delta function, the 1-D transducer PSF might be viewed as some hypothetical finite length pulse sequence. The spatial impulse response taken along one direction will be referred to as a *one dimensional reflectivity function*. Assuming scatterers on each RF-sequence are located on a uniform grid and the system impulse response (ultrasonic pulse) is shift invariant along each RF-line, the beam former gives a single receive signal that is given by $$g[n] = s[n] * f[n] + u[n] \qquad (1.2)$$

Here $u[n]$ is the additive white noise perturbing the received RF signal $g[n]$. The influence of the convolutional kernel $s[n]$ results in "deformation" of the useful information about $f[n]$ and it is one of the factors giving rise to appearance of the speckle noise. The speckle noise affects the quality ultrasonic images in which it is present by reducing the contrast, lowering the signal to noise ratio (SNR) and obscuring important diagnostic details. Thus, the task of recovering of the reflectivity function $f[n]$ from the received signal $g[n]$ is of great importance. Generally speaking, this problem is more complicate, because the system impulse response $s[n]$ cannot be considered to be available. The absorption of the ultrasound energy in tissues increases with the pulse frequency. This frequency-dependent attenuation process causes to both the pulse amplitude and shape to be dependent on depth in tissue and leads to the observed non-stationarity of RF-sequences. So, the problem of the reflectivity function derivation or, the same, the problem of tissue characterization can be reformulated in term of the *blind deconvolution problem*. One way to deal with the non-stationarity is to break up the RF-sequence into a number of (possibly overlapping) segments, such that it will be possible to state that within each one the frequency-dependent attenuation process does not affect the pulse spectrum properties considerably [3]. In such a case it is possible to treat a given RF-sequence separately by the performing the deconvolution procedure for each segment. Finally, the deconvolved segments can be integrated together supplying us the entire processed RF-sequence. A problem that could arise in such approach is that short data intervals may not contain enough data for precise estimation. The pulse estimation method proposed in this paper is tolerative enough to the data point insufficiency problem, and so, it was decided to use the above-mentioned "segment-wise" processing.

Our method is based on the homomorphic analysis of the RF-sequence spectrum [7], but in the proposed algorithm we do not use the wide-accepted cepstrum-based technique [2,4-6]. It has been shown [7] that for any signal of finite duration its complex cepstrum always extend to infinity. Consequently, using the discrete Fourier transform for its calculation always gives rise to aliasing errors. The cepstrum aliasing can be reduced (but not avoided) by zero padding of the RF-sequences. It also can be noted, that the setting the high sampling rate (it is intended to decrease aliasing errors in the reflectivity function spectrum estimation), increases the degrading effect of the measurement noise on the cepstrum estimates. The higher the sampling rate, the wider the spectrum band, occupied almost exclusively by the noise. This band has to be included to the cepstrum computation and, consequently, it causes significant errors in the estimation of the cepstrum and unavoidably in the estimation of the ultrasonic pulse. Another inconvenience is the fact, that for signal lengths about 512 sample points (that is usually used for such algorithms) the probability that most complex zeroes will be located close to the complex unit circle is large, and it leads to instability of all cepstrum-based methods. To remove this instability exponential weighting with a factor $\alpha < 1$ is used, but unfortunately such weighting can give artifacts in the estimation of the ultrasonic pulse function. Computation of the 1-D ideal low-pass filter parameters in the cepstrum domain also can be considered to be a quite problematic task, because it has to be changed systematically from some initial estimate to find optimal values giving the best deconvolution results for a given probe.

All the above-discussed problems related to the cepstrum based processing brought us to another method for the ultrasound pulse estimation. The ultrasound pulse spectrum is recovered using the Wavelet analysis of the RF-sequence log-spectrum and reconstructed from the Wavelet transform coefficients. After the pulse estimation the problem, expressed by (1.2), is reduced to a deconvolution problem as a special case of the inverse problem. This inverse problem can be solved in the LS sense, but its direct solution is impossible due to the spectral properties of the autocorrelation matrix to be inversed. Thus, some regularization technique should be used. In order to implement such inverse, instead of estimating the $f[n]$, we find its stable moment (approximation) $\langle f, w \rangle$, where $w$ is a suitable mollifier, that can be, in Wavelet language, a scaling function or a wavelet. Such approach is called the *approximate inverse* and it is explicitly explained in [10].

The proposed blind deconvolution algorithm based on the Wavelet transform technique is tested in 1-D deconvolution of computer simulated data and *in vitro* ultrasound data in the radial direction. It was shown that its performance remains stable for severe noise levels and obtained results are very correlative with the tested reflectivity functions.

Section 2 gives a brief discussion of the signals and its spectra. A surface description of the homomorphic analysis is also given here. Section 3 exclusively deals with the main ideas of the Wavelet analysis and its use for the non-parametric pulse estimation algorithm derivation. Section 4 gives an overview on ill-posed inverse problems and introduces a method for construction of the approximate inverse filter.

Finally, Section 5 demonstrates results of using the approach to recovering computer simulated reflectivity functions and reflectivity functions of ultrasound phantoms.

2. ULTRASOUND SIGNALS AND HOMOMORPHIC ANALYSIS

The frequency-dependent attenuation process appears as decrease with distance of the mean frequency and the amplitude of the ultrasonic pulse. So, it is unacceptable to estimate the pulse using the whole data, as in this case it may lead to serious estimation errors. It might be appropriate to break up the RF-sequence into some number of (possibly overlapping) segments and to state that within each one the frequency-dependent attenuation process does not affect the pulse spectrum properties strongly. In this light, we can implement the deconvolution procedure inside of each segment. The final result (i.e., processed image line) might be seen as an integration of the segments after the treatment. The model of the entire RF-line [3] can be as follows $$g[n] = \sum_{k=1}^{M} f[n-k]s[k,n-k] + u[n], \quad n = 1,2,...,N \quad (2.1)$$

In this expression $g(n)$ is a received RF-sequence, $f[n]$ is a reflectivity function, $u[n]$ is the additive white noise term, and $s[k,n]$ is the ultrasonic pulse ascribed to the point $n$. It was assumed that despite of the pulse dependence on the RF-line segment "depth", it could be modeled as $M$-points finite length sequence. The finality of the above sum also assumes that $f(n)$ is a sequence with length no longer than $N$ points.

To turn the problem to be locally stationary, we assume that the pulse statistic is unchangeable on intervals $(n_{i-1}, n_i]$, for $i = 1,2,...,I$, $n_0 = 0$, $n_I = N$. It says that $s_i(k) = s(k,n)$, $n_{i-1} < n < n_i$. We set $$f_i[n] = \begin{cases} f[n], & n_{i-1} < n < n_i \\ 0, & \text{otherwise} \end{cases}.$$

For these assumptions the model (2.1) can be written as $$g[n] = \sum_{i=1}^{I} \sum_{k=0}^{M} f_i[n-k] s_i[k] + u[n]. \qquad (2.2)$$

So, we start the algorithm derivation for one convolution segment of the above sum that can be modeled by the equation (1.2). This equation can be specified in the frequency domain by taking the Fourier transform on both its sides.

$$G(\omega) = F(\omega) S(\omega) \qquad (2.3)$$

There are certain interesting observations that can be made for (2.3). Of interest here is the fact that the RF-sequence spectrum is obtained as a result of the multiplying the pulse spectrum by the reflectivity function spectrum and they are quite different regarding its statistical properties. One of the most acceptable models for the ultrasonic pulse sequence is such in which it is defined as a smooth Gaussian-like function multiplied by an exponential of certain phase [11]. The frequency-dependent attenuation process influences the pulse spectrum, and consequently, its time pattern, but it is reasonable to expect that this influence is smooth with depth. It implies that, regardless the reflection depth, the pulse spectrum should be a smooth, "slow" function with a maximum in vicinity of the nominal resonance frequency of the transducer. Such a spectrum cannot admit considerable ruptures or spikiness.

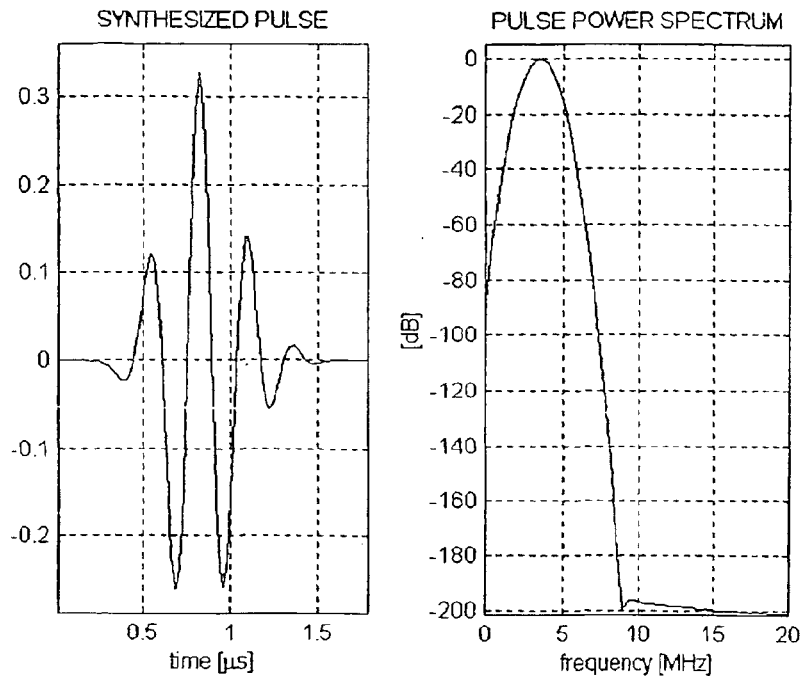

Figure No1: *Measured pulse and its power spectrum*

In Figure No1 one can see the pulse-echo signal received from a planar reflector in a water tank. Assuming that the reflectivity function of this elementary reflector is a zero sequence with only one weighted digital delta with appearance at the point appropriate to the "two-flight" time, the echo signal is to be close to our ultrasonic pulse.

One can see that the results presented in Figure No1 are in a good agreement with the above mentioned pulse model and the conclusions about the pulse spectrum character. In order to conduct these measurements the ultrasonic transducer and quadrilateral thick perspex stick used as a planar reflector were immersed into a water tank. The transducer was the standard case style Panametrics V384 3.5/0.25 MHz with diameter of 0.46". The Panametrics computer controlled pulser-receiver (model 5800) was used to excite it. The target was located in the distance lightly longer than the transducer nominal focus length (4.515"). The obtained echoes were received and digitized at 50 MHz using the Tektronix TDS-420 digital oscilloscope. The other half of the story is the reflectivity function and its spectrum. It is well understood that the reflectivity function ascribed to speckled regions (soft tissue) of ultrasound images may be an irregular, spiky, and although a normal distributed random function exhibiting complexity of the underlying tissue structure [5]. Another approach to the tissue reflectivity modeling is to assume that it may admit some form of layered structure. This implies that the reflectivity function will be sparse, i.e. only a limited number of samples have nonzero value [3]. Let us to omit the discussion of what model is more appropriate, because of importance here is that there is a common point for both. Such reflectivity sequences will have very irregular, spiky spectrum with numerous ruptures and dips. Moreover such a spectrum should be broadband in contrast to the pulse spectrum. Hence the RF-sequence spectrum is nothing more than a result of the multiplication of the irregular, "wild", broadband reflectivity spectrum by the relatively smooth and band-limited spectrum of the ultrasonic pulse. In Figure No2 one can see a simulated spectrum of the reflectivity function and a typical spectrum of the measured RF-sequence taken in logarithmic scale.

Now, let us consider the complex logarithm of the $G(w)$ in (2.3). The Fourier transform of the RF-sequence (i.e., Z-transform evaluated on the unit circle) can be defined in terms of its amplitude and argument $G(w) = |G(w)| \cdot e^{j \cdot \arg(G(w))}$. In the same manner, let us define $S(w) = |S(w)| \cdot e^{j \cdot \arg(S(w))}$ and $F(w) = |F(w)| \cdot e^{j \cdot \arg(F(w))}$. Then the complex logarithm of the $G(w)$ is defined as

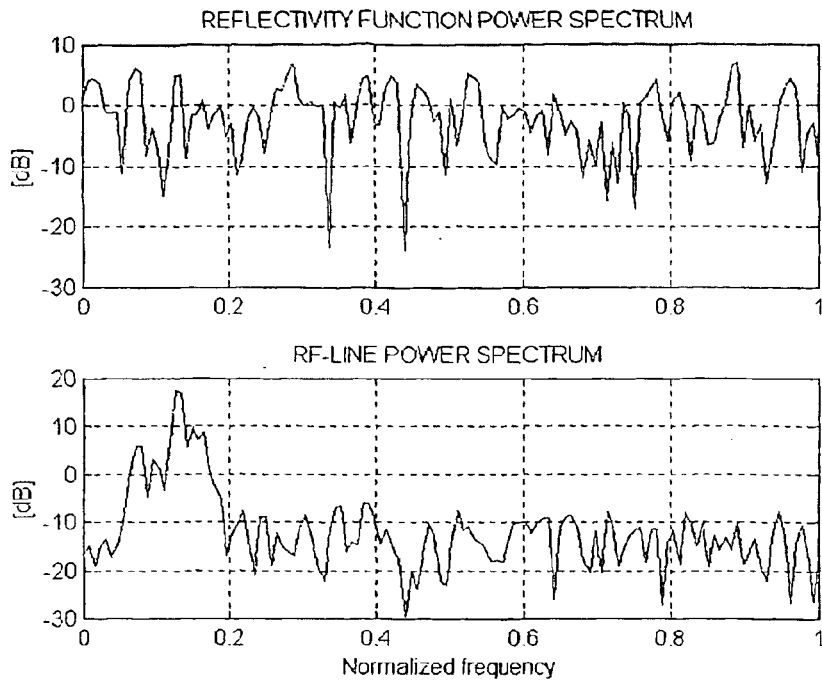

Figure No2: *Power spectra of the simulated reflectivity function and the typical RF-sequence in logarithmic scale.*

$$log\{G(\omega)\} = log\{|G(\omega)|\} + j\,arg[G(\omega)] = log\{S(\omega)\} + log\{F(\omega)\} = \\ = log\{|S(\omega)|\} + j\,arg[S(\omega)] + log\{|F(\omega)|\} + j\,arg[F(\omega)]$$

(2.4)

It implies that $$log\{|G(\omega)|\} = log\{|S(\omega)|\} + log\{|F(\omega)|\} \\ arg[G(\omega)] = arg[S(\omega)] + arg[F(\omega)]$$

(2.5)

The above relationships (2.4) and (2.5) are well known in the homomorphic signal processing. Now, one can see that the log-amplitude of the $G(w)$ can be represented as a sum of two components, namely, the smooth and regular log spectrum of the ultrasonic pulse and very jagged and irregular log-spectrum of the reflectivity function. Moreover, if we glance at these functions from a point of its scales, it will be clear that $log\{|S(\omega)|\}$ is much "slower", than $log\{|F(\omega)|\}$ and it implies that its scales are quite different. Hence, it is reasonable to assume that its frequency spectra (i.e., frequency spectra of the log-spectra) do not overlap significantly and one can separate the two components or perform independent processing of the two components. Moreover, a low frequency pole (slowly varying component) and a high frequency plateau (rapidly varying component) typically characterize the Fourier transform of $log\{G(\omega)|\}$. This fact is used in the cepstrum-based methods for the deconvolution, whose comprehensive description can be found in [4,7]. It already was pointed out in Section 1, that there are a number of inconveniences related to it. The main problems are intrinsic infinity of the cepstrum leading to aliasing errors when using discrete Fourier transform for its computation; sensitivity of the cepstrum to the out-of-band noise; necessity to compute the minimum phase and maximum phase cutoff values for the ideal filter in the cepstrum domain. All this brought us to proposal of another methods based on the principles of the homomorphic deconvolution without entering the cepstrum domain.

Thus, to estimate the pulse log-spectrum we must to filter out the irregular jagged component of the RF-sequence log-spectrum and for this purpose the Wavelet analysis was used. The wavelet method "acts as a mathematical microscope in which we can observe different scales of the signal by just adjusting the focus". In the given case we are looking for a long-term, slow portion of the log spectrum. Such changes might be better analyzed with a smooth, regular wavelet. In this work the "Coiflet" family of wavelets have been employed.

3. MAIN IDEAS OF THE WAVELET ANALYSIS AND ITS USE FOR THE PULSE ESTIMATION

We are far from the introducing this theory, but let us just highlight a few basic points of this powerful, beautifully structured analysis, in order to supply an intuitive platform for the derivation of the pulse estimate algorithm.

The wavelet transform is defined by decomposing the signal into a family of functions, which are the translations, and dilations of a unique function $\psi(x)$. The function $\psi(x)$ is called a *wavelet* and the corresponding wavelet family is given by $\{\sqrt{s}\,\psi(s(s-u))\}$, where $(s,u) \in \Re^2$ [12]. The wavelet transform of a function $f(x) \in L^2(\Re)$ is defined by $$Wf(s,u) = \int_{-\infty}^{\infty} f(x)\sqrt{s}\,\psi(s(x-u))\,dx \qquad (3.1)$$

In order to reconstruct the analyzed signal from its Wavelet transform, the Fourier transform of the wavelet function should satisfy the following admissibility condition $$C_\psi = \int_0^\infty \frac{|\hat{\psi}(\omega)|^2}{\omega}\,d\omega < \infty \qquad (3.2)$$

It implies that $\hat{\psi}(0) = 0$, and that $\hat{\psi}(\omega)$ is small enough in vicinity of $\omega = 0$. If we denote $\tilde{\psi}_s(x) = \psi_s(-x)$, where $\psi_s(x) = \sqrt{s}\,\psi(sx)$, then we can rewrite the Wavelet transform at a point $u$ and a scale $s$ as a convolution product with $\tilde{\psi}_s(x)$ $$Wf(s,u) = f * \tilde{\psi}_s(u) \qquad (3.3)$$

The resolution of the Wavelet transform varies with the scale parameter $s$. The Wavelet transform decomposes the signal into a set of frequency bands having a constant size on a logarithmic scale [13]. The smaller the scale, the courser the resolution in the spatial domain and fine in the frequency domain, and vice versa. We can derive that the reconstruction of $f(x)$ from $Wf(s,u)$ is given by $$f(x) = \frac{1}{C_\psi} \int_{-\infty}^{\infty}\int_0^{\infty} Wf(s,u)\,\psi_s(x-u)\,ds\,du \qquad (3.4)$$

Like a window Fourier transform a Wavelet transform is redundant. In other words, its value at a given point of the phase (time-frequency) space depends on its values at neighboring points of the phase space.

In order to overpower the transform abundance, the Wavelet transform can be discretized by sampling both the scale parameter and the translation parameter. By choosing the scale parameter sampling to be exponential, and the translation parameter sampling to be proportional to the former, the discrete Wavelet transform is defined by $$W_d f(j,n) = Wf(a^j, \frac{nb}{a^j}) = \int_{-\infty}^{\infty} f(x)\, \psi_{a^j}(x - \frac{nb}{a^j})\, dx =$$
$$= f * \tilde{\psi}_{a^j}(\frac{nb}{a^j}), \qquad a\text{ -delation step} \qquad (3.5)$$

The choosing the scaling parameter $a$ to be 2 and $b$ to be 1 provides a very important particular case of the Discrete Wavelet transform. It was proved that there exist some wavelets $\psi(x)$ such that $(\sqrt{2^j}\,\psi(2^j(x-2^{-j})))$, where $(j,n) \in Z^2$, is an orthonormal basis of $L^2(\Re)$. These particular wavelets are called *orthogonal wavelets*. In such case, any function can be reconstructed from its decomposition into a Wavelet orthonormal basis with the classical expansion formula of a vector into an orthonormal basis $$f(x) = \sum_{j \in Z} \sum_{n \in Z} \langle f(u), \psi_{2^j}(u - n2^{-j}) \rangle \, \psi_{2^j}(u - n2^{-j}). \qquad (3.6)$$

One can define the vector space $V_{2^j}$ composed from the set of all possible approximations of functions at the resolution $2^j$. The sequence of vector spaces $(V_{2^j})_{j \in Z}$ is called a *multiresolution approximation* of $L_2(\Re)$. For any function $f(x)$ at the resolution $2^j$ is given by the orthogonal projection of $f(x)$ on $(V_{2^j})_{j \in Z}$. An orthonormal basis of $V_{2^j}$ can be built by dilating and translating a particular function $\phi(x)$ called a scaling function. The family of functions $(\phi_{2^j}(x - 2^{-j}n))_{n \in Z}$ is then the orthonormal basis of $V_{2^j}$. The function $\phi(x)$ can be viewed as a low pass filter; therefore the discrete approximation of $f(x)$ (i.e. its orthogonal projection into $(V_{2^j})_{j \in Z}$) can be computed as $$A_{2^j} f = (f * \tilde{\phi}_{2^j}(2^{-j}n)) = \langle\langle f(x), \phi_{2^j}(x - 2^{-j}n) \rangle\rangle_{n \in Z} \qquad (3.7)$$

Here the function $\tilde{\phi}(x)$ is a reflection of the function $\phi(x)$.

The difference of information between the approximations as the resolutions $2^j$ and $2^{j+1}$ (i.e., the details of the function at the resolution $2^j$) are equal to the orthogonal projection of $f(x)$ on the orthogonal complement of $V_{2^j}$ in $V_{2^{j+1}}$. Let us denote this complement space as $O_{2^j}$. The family of functions $(\psi_{2^j}(x-2^{-j}n))_{n \in Z}$ is the orthonormal basis of $O_{2^j}$. When the resolution $2^j$ varies in the interval $(0, \infty)$ the functions $(\psi_{2^j}(x-2^{-j}n))_{n \in Z}$ constitutes a *wavelet orthonormal basis of* $L_2(\Re)$ [12]. The difference of information between the approximations as the resolutions $2^j$ and $2^{j+1}$ can be computed by expanding the $f(x)$ into the orthonormal basis of $O_{2^j}$ and it is characterized by the set of inner products $$D_{2^j} f = (f * \tilde{\psi}_{2^j}(2^{-j}n)) = \left(\langle f(x), \psi_{2^j}(x-2^{-j}n)\rangle\right)_{n \in Z} \qquad (3.8)$$

The Fourier transforms of $\phi(x)$ and $\psi(x)$ are characterized by the following relations $$\hat{\phi}(\omega) = \prod_{k=1}^{\infty} H(e^{-i2^{-k}\omega}), \quad \hat{\psi}(2\omega) = G(e^{-i\omega})\hat{\phi}(\omega)$$
$$\text{where} \quad G(e^{-i\omega}) = e^{-i\omega}H(e^{-i\omega})$$
(3.9)

In the above expressions the filters $G$ and $H$ make a pair of *quadrature mirror filters*. So, it is was proved, that $A_{2^j}f$ and $D_{2^j}f$ can be computed by a algorithm that is in fact a classical scheme known in the signal processing community as the *quadrature mirror filter bank decomposition* or *subband coding* [14].

Now we can come back to the subject of our discussion. It was shown that the log-spectrum of the RF-sequence is combined from the regular, smooth log-spectrum of the pulse and the irregular, jagged log-spectrum of the reflectivity function. Thus, it was concluded that from the scale point of view these signals are quite different. As a consequence of this fact it is reasonable to expect that there is a resolution level $2^j$ in which the approximation of the analyzed signal $A_{2^j}f$, where $f = \log\{|G(w)|\}$, characterizes the low-frequency components of $f$, dominated by $\log\{|S(w)|\}$. In the same time, the details bear information, related to the jagged, high frequency components of the signal, induced by $\log\{|F(w)|\}$. If we decide $J$ to be the desired resolution level, then the analyzed log-spectrum of the RF-sequence can be decomposed as follows $$f = \log\{|G(w)|\} = A_{2^J} f + \sum_{j \leq J} D_{2^j} f. \qquad (3.10)$$

In the above expression we assume the pulse log-spectrum dominates in the first term, while the reflectivity log-spectrum dominates in the second.

In order to verify our assumption a $2^8$-point RF-sequence was simulated according to (1.2). The pulse was defined as an exponential with a linear time-weighted Gaussian-like envelope and the reflectivity was simulated as a function consisting of the digital delta functions with random appearances and weights. Both the weights and the appearances were taken from the normal Gauss distribution. In Figure No3 one can see the generated function and the logarithm of its Fourier transform. In order to decompose $\log\{|G(\omega)|\}$ a wavelet filter of order 5 from the Coiflet Wavelets family was chosen. It is a wavelet with support width of 29 points and the filter length of 30 points. This wavelet is an orthogonal compactly supported and it has a highest number of vanishing moments for both the scaling and wavelet functions (i.e., the vanishing moment's number for $\phi(x)$ is 30 and the vanishing moment's number for $\psi(x)$ is 29). The maximal decomposition level was chosen to be 4 and the decomposition was performed using the Fast Wavelet Transform algorithm [14].

In Figure No4 one can see results of the decomposition. Note, that at this stage we intentionally did not add any noise to the simulated signal in order to clarify the results and, consequently, the main idea of the approach. The noise will be added at the next stage and an appropriate method for its cancellation will be proposed.

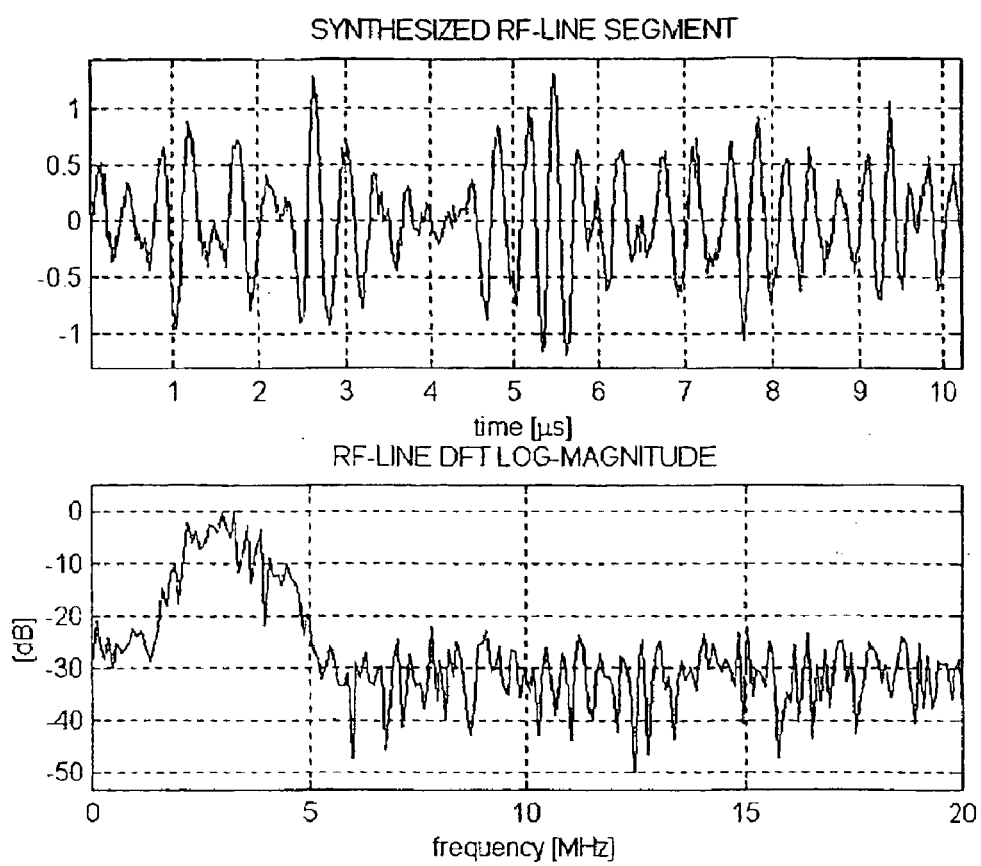
Figure No3: *Synthesized RF-sequence and its Fourier transform log-amplitude*

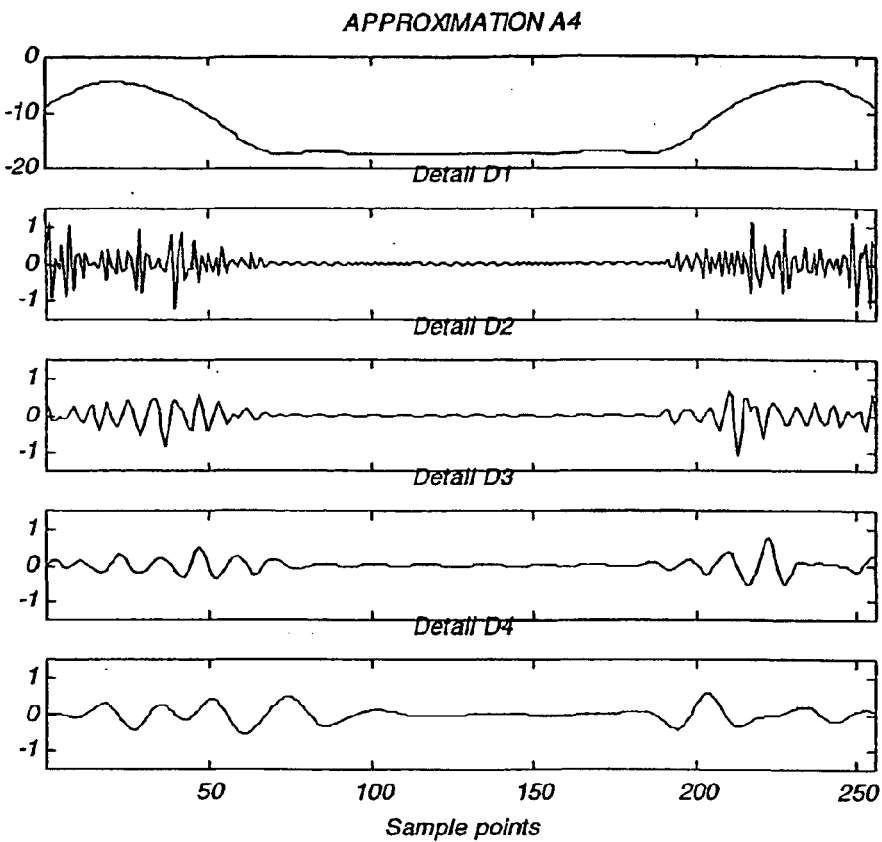

Figure No4: *The Wavelet of level 4 of the Fourier transform modulus of the synthesized RF-sequence*

Figure No4 gives a clear picture of what happens in process of the decomposition. It is obvious that the fourth level approximation of the RF-sequence log spectrum is quite smooth and regular. All the high frequency information (i.e., ruptures, dips and spikiness of the spectrum) is included into the details of this decomposition. In order to verify whether the obtained approximation is close to the log spectrum of the pulse, in Figure No5 both spectra (i.e., estimated and original) are plotted together. No doubts that our assumption is precise enough. Thus, an important conclusion to be made here is that the amplitude of the ultrasonic pulse spectrum can be recovered from the approximation coefficients of the Wavelet transform of the RF-sequence log spectrum.

Now, we have to confirm the algorithm performance when the noise component of the (2.1) is not zeroed. The simplest method to reduce out-of-band noise influence on the estimation process is to use a one-dimensional low-pass filtering of all RF sequences in the radial direction. It is also possible to use the classical Wiener filter. In Figure No6 the block-diagram of our process is viewed. We denote by $g_0[n]$ RF-sequence before the noise addition.

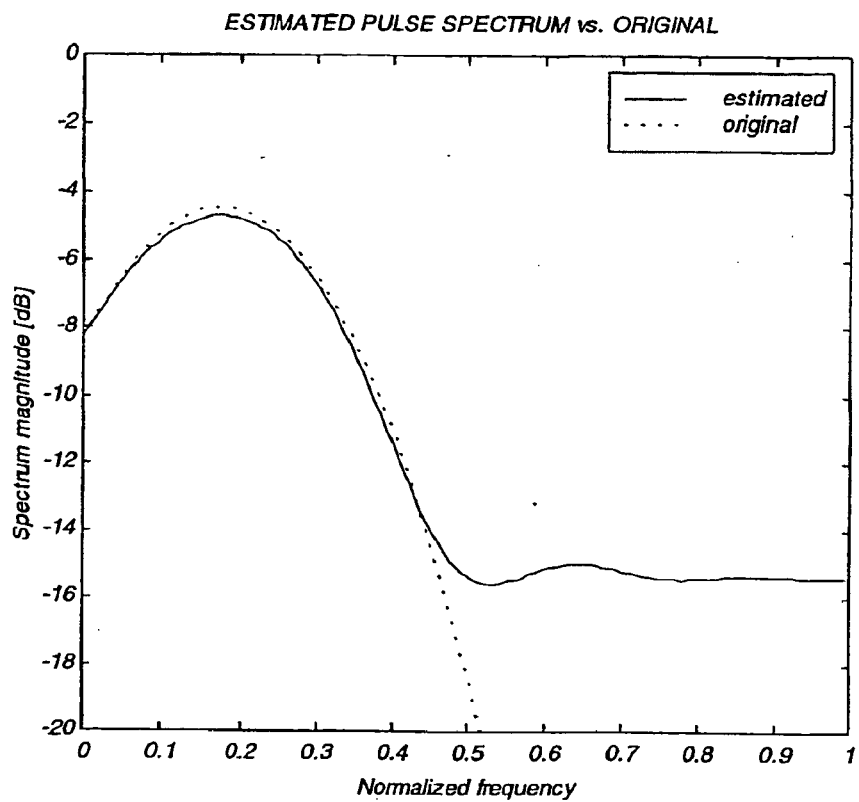

Figure No5: *Estimated pulse's Fourier transform amplitude (continuous line) vs. original one (dashed line)*

It is easy to show that the frequency response $H(\omega)$ of the optimal filter, with impulse response $h(n)$, minimizing the variance $E\{(g[n] - g_0[n])^2\}$ is given by [15]

$$H(\omega) = \frac{|S(\omega)|^2}{|S(\omega)|^2 + \sigma_u^2/\sigma_f^2} \tag{3.11}$$

In the above expression $S(\omega)$ is the frequency response of the ultrasonic pulse, $\sigma_u^2$ is the noise variance, and $\sigma_f^2$ is the reflectivity function variance. Note that it is valid in speckled regions of the RF-image, where the reflectivity function elements can be defined as independently identically distributed. Otherwise, in place of $\sigma_f^2$ we have to use $|F(\omega)|^2$, that is the power spectral density of $f[n]$.

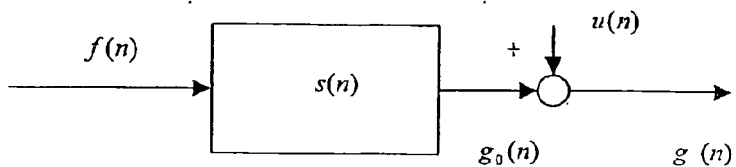

Figure No6: *The block diagram of the studied process.*

Since in the beginning of the processing $S(\omega)$ is unknown one can divide the filtering procedure into the two stages: deriving the first estimate of the pulse spectrum from RF sequence filtered by a low-pass filter (out-of-band noise cancellation) by using the first stage results filtering the RF sequence by the optimal Wiener filter given in (3.11) and, consequently, to compute the second, more precise estimate of the pulse spectrum The second scheme performance might give us a more robust filtering, but at the expense of greater computations. In our experiments, the former filtering scheme has been chosen.

Now we are about to get the pulse estimation in the time domain, but before it, the pulse Fourier transform phase must be computed. In certain cases it is reasonable to assume the pulse is a minimum phase sequence. For rational systems it is equivalently to saying that all zeros and poles are inside the unit circle [7]. This requirement implies that the terms $log|S(e^{j\omega})|$ and $arg[S(e^{j\omega})]$ constitute the Hilbert transform pair, and as a consequence of the fact, $arg[S(e^{j\omega})]$ can be computed from $log|S(e^{j\omega})|$. Namely, knowing $log|S(e^{j\omega})|$, that is the real part of the Fourier transform of the complex cepstrum of the pulse, allows us to compute the even (symmetric) part of the latter. This even part is the real cepstrum. If the ultrasonic pulse is minimum phase sequence, then its complex cepstrum decidedly real, causal sequence. Consequently, it completely defined by its even part, in other words, by its real cepstrum. So, in the case of minimum phase (or maximum phase) pulses we can obtain the complex cepstrum from the real cepstrum, and practically it is computed by multiplying the real cepstrum with the following window $$u_+[n] = \begin{cases} 0, & n < 0 \\ 2, & n > 0 \\ 1, & n = 0 \end{cases} \qquad (3.12)$$

At this point the reader could be a bit confused, because we clearly contradict ourselves. One of the motivations of the algorithm proposal was the desire to avoid possible aliasing errors in the cepstrum domain, and now we use it to reconstruct the pulse Fourier transform phase. In our opinion, there is no significant contradiction here, since $log|S(e^{j\omega})|$ is quite smooth, "slow" function, and as a consequence of the fact, its cepstrum is fairly concentrated in vicinity of the origin. Thus, it is unreasonable to expect here considerable aliasing errors.

Note that the assumption of the minimum phase pulse is very hard and might seem unrealistic. Yet it was proved that in many cases it is valid and can be used for the pulse estimation purposes. Moreover, one can use exponential weighting of the RF-sequence, and in such a case the convolution in (1.2) is equal to a convolution of two sequences weighted exponentially. The zeros and poles of such a sequence are shifted radially by the factor reciprocal to the exponential basis. Thus, the exponential weighting is a useful technique for converting a mixed phase signal to a minimum-phase or a maximum-phase signal [7].

To verify the said above in Figure No7 the ultrasonic pulse and its minimum phase version are plotted together. It is obvious that the minimum phase assumption is not less basis. At this light, the proposed pulse estimation algorithm can be combined from two stages. At the first stage, we compute an approximation of amplitude of RF-sequence Fourier transform and it supplies us an estimate of the pulse Fourier transform amplitude. At the second stage, the pulse complex cepstrum is computed and, consequently, the pulse is estimate in the time domain.

Now, we test the algorithm performance on synthetic data generated according to (2.1). The ultrasound pulse was minimum phase and its parameters were chosen as close as possible to ones of the measured ultrasound pulse (Figure No7). The reflectivity was simulated as a function consisting of the digital delta functions with random appearances and weights. The signal-to-noise ratio was chosen to be approximately 7 dB and it is given by $$SNR = 10 \cdot \log\left[\frac{\sigma^2_{signal}}{\sigma^2_{noise}}\right] \quad (3.13)$$

Here $\sigma^2_{signal}$ and $\sigma^2_{noise}$ the signal and noise variances, respectively.

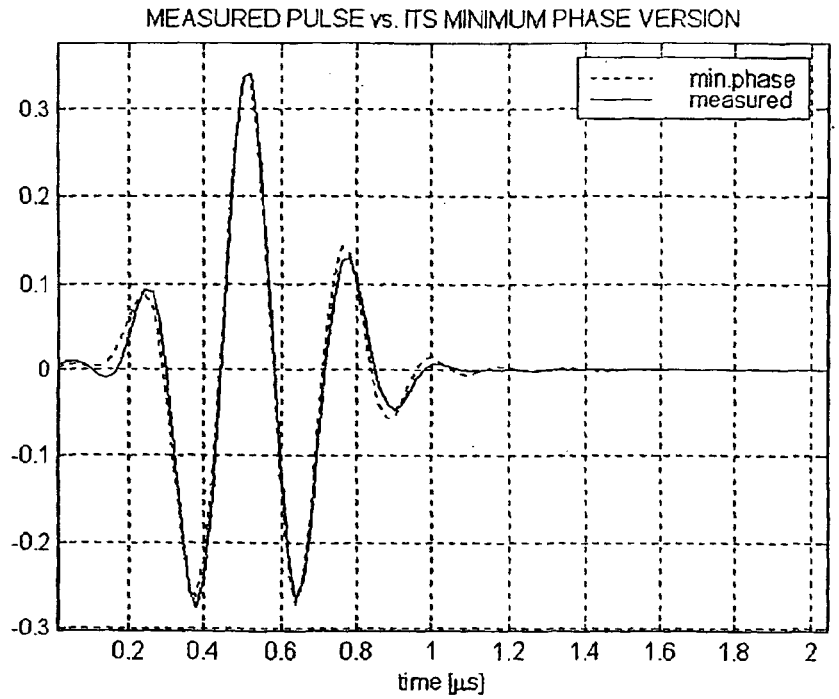

Figure No7: *Measured pulse and its minimum phase reconstruction*

The estimation results are viewed in Figure No 8. On the left-hand side picture one can see eight pulse estimates performed on eight different data segments. On the right-hand side picture the original pulse is viewed. Note that the estimation algorithm does not require any initial conditions or parameters, except of the analyzing wavelet and the decomposition level choice. In Figure No 9 the original pulse is plotted vs. the averaged (from the previous eight pulses) estimated pulse.

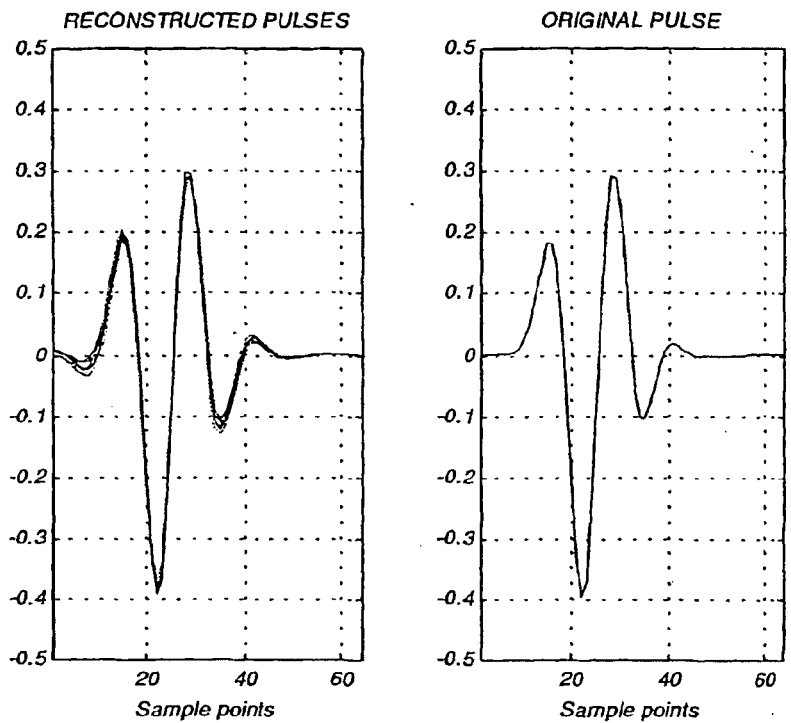

Figure No8: *8 pulses estimated from synthesized data contaminated by the white noise of, approximately, 7 dB (left); original pulse (right)*

The pulse estimation algorithm performance was tested on the real data set. The RF-sequences were obtained using the standard case style transducer (Panametrics V384 3.5/0.25 MHz with diameter of 0.46"). The obtained echoes from a phantom, *which specific structure will be described in Chapter 5 of the paper*, were received and digitized at 50 MHz. An entire RF-sequence was divided into shorter sections. The number of samples per section was 256. In Figure No10 one can see ultrasound pulse estimated from five different RF-sections (left-hand side).

It can be seen that all the estimated pulses possess a similar form, resembling the ultrasound pulse, measured experimentally. The variations among the estimated pulses may be ascribed to the statistical estimation errors, "coloration" of the reflectivity function (i.e., it might not be statistically white sequence), and contribution from some effects of the medium having spatially varying characteristics (such as aberration, for example). On the right-hand side of Figure No10 averaged estimated pulse is viewed versus the measured ultrasound pulse, and it can be seen that they are very close one to another. Additionally it is reasonable to assume that the pulse in adjacent lines is same, so an average pulse can be found for a number of lines. This averaging can be accomplished either in the wavelet, Fourier or time domains and it is intended to decrease the estimate variance.

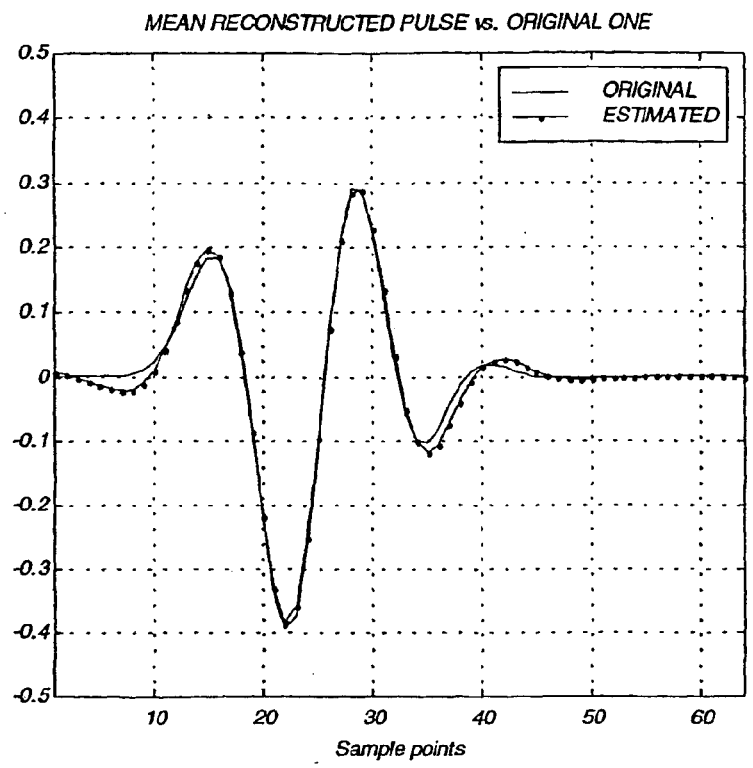

Figure No9: *Average estimated pulse versus original pulse*

After the pulse estimation, the problem presented in (2.1), as the blind deconvolution problem, becomes a classical inverse (deconvolution) problem. This procedure ultimately relies on knowledge of the pulse and its preciseness. The pulse estimation stage was performed with moderate errors, and, consequently, it is reasonable to except that the following stage (deconvolution procedure) will be not disturbed significantly by errors caused by the low acuteness of the first stage.

The next section deals exclusively with the inverse problem solution. It will be shown how it is possible to stabilize its solution by the approximate inverse technique. Results of simulations and *in vitro* experiments will be shown also.

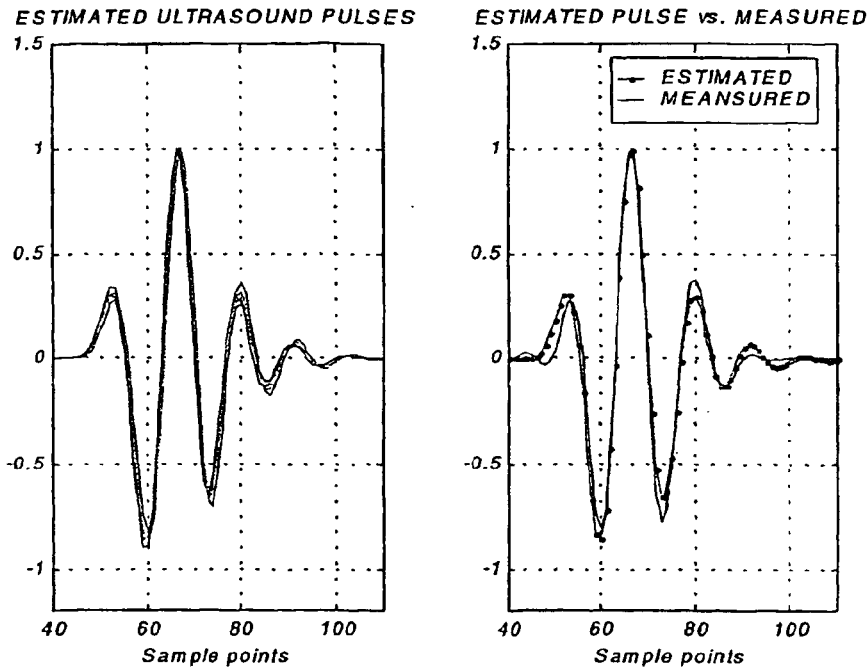

Figure No10: *Pulses estimated from the real data set (five RF-lines obtained from the tissue-mimicking phantom) [left-hand side picture]; averaged pulse (dotted line) vs. measured pulse [right-hand side picture]*

4. APPROXIMATE INVERSE FOR ILL-POSED PROBLEMS AND ITS USE FOR THE REFLECTIVITY FUNCTION ESTIMATION

Ignoring the noise term the equation (2.1) can be viewed as an operator equation $Sf = g$, where $S$ is assumed to be linear operator between the Hilbert spaces $X$ and $Y$. In our case the operator $S$ is the convolution operator and its structure will be described below.

It is well understood that the multiplication of $f$ by $S$ is a smoothing operation that tends to dampen high-frequency components in $f$, such that the function $g$ is a smoother function than $f$ [16]. Thus, the deconvolution process can be expected to amplify the high-frequency components, and if the data was perturbed by noise, this deconvolution process becomes highly unstable. The larger the frequency, the larger perturbations of the desired solution. So, regularizing techniques are needed to stabilize the finding the optimal solution and it is a matter of this section.
Singular value decomposition of square matrix A is defined as $$S = U \Lambda V = \sum_{i=1}^{n} u_i \lambda_i v_i \qquad (4.1)$$

The two matrices $U$ and $V$ are orthogonal ($U^T U = V^T V = I$) and consist the left and right singular vectors. The middle matrix is a diagonal matrix and its diagonal elements are nonnegative singular values of matrix $A$ ordered in non-increasing order. The well-known definition of the condition number of $S$ is given as $$\|S\|_2 \|S^{-1}\|_2 = \frac{\lambda_{max}}{\lambda_{min}} \qquad (4.2)$$

Here $\lambda_{max}$ and $\lambda_{min}$ are maximal and minimal singular values respectively.
The well-known solution of the linear equation expressed in terms of the SVD is obtained as follows $$g = \sum_{i=1}^{n} \langle u_i^T g \rangle u_i, \qquad f = \sum_{i=1}^{n} \langle v_i^T f \rangle v_i \qquad (4.3)$$

Thus we obtain $$f^* = \sum \frac{u_i^T g}{\lambda_i} v_i \qquad (4.4)$$

The singular values of the matrix $S$ decay gradually to zero, consequently the condition number is approximately reciprocal of the machine precision, i.e. almost infinite, thus matrix $S$ is singular.
The most prominent regularization method for ill-posed problems is Tikhonov – Philips regularization, where the error norm is penalized with *a priori* information on the solution. For the sake of simplicity we use the $L_2$– norm of the solution and get $$\varepsilon^2 = \{\|Sf - g\|_2^2 + \gamma \|f\|_2^2\} \to min \qquad (4.5)$$

The minimum of this functional is computed as solution of $$(S^T S + \gamma I)f_\gamma = S^T g \qquad (4.6)$$

Parameter $\gamma$ is a regularization parameter and when it approaches zero we obtain the original, non-regularized solution.

One can express $f_\gamma$ in terms of the SVD of matrix $S$ as follows $$f_\gamma = \sum_{i=1}^{n} F_\gamma(\lambda_i) \lambda_i^{-1} (u_i^T g) v_i, \quad where \quad F_\gamma(\lambda_i) = \frac{\lambda_i^2}{\lambda_i^2 + \gamma}$$

The factors $0 \leq F_\gamma(\lambda_i) \leq 1$ are called the Tikhonov filter factors and they control the damping of the individual SVD components of the regularized solution [17].

One can show that this regularization method is a special case of the *approximate inverse*. Approximate inverse means a solution operator, which maps the data $g$ to a stable approximation of the solution of the ill-posed problem $Sf = g$. This inversion operator (stable inverse filter) can be precomputed without using $g$. Thus, we compute instead of $f$ its stable moment $\langle f, e_\gamma \rangle$, where $e_\lambda$ is a suitable mollifier. This mollifier may be a low-pass filter, or in wavelet language a scaling function or a wavelet. Consequently, the high-frequency components of $f$ which are mostly affected by noise are reduced. The computation of $\langle f, e_\gamma \rangle$ is achieved by approximating $e_\lambda$ in the range of the operator $S^T$ by the reconstruction kernel (inverse filter) $v_\gamma$, where $S^T \cdot v_\gamma = e_\gamma$. In such a case the following relationship takes place $$\langle f, e_\gamma \rangle \approx \langle f, S^T v_\gamma \rangle = \langle Sf, v_\gamma \rangle = \langle g, v_\gamma \rangle \qquad (4.7)$$

Here we assume the equation $S^T v_\gamma = e_\gamma$ to be solvable, but if it is not, then one can approximate $v_\gamma$ by minimizing the defect $\|S^T v_\lambda - e_\gamma\|$. This minimization problem leads to solution of the following linear equation system $$S S^T v_\gamma = S e_\gamma \qquad (4.8)$$

There are diverse approaches to solve (4.8). It can be done by direct inverse, or iteratively [16], or in the spectral domain [15]. Of importance here the fact that only light regularization (relatively small parameter $\gamma$ for the Tikhonov approach, for example) is needed to find the optimal $v_\gamma$.

Now, let's come back to the deconvolution. If we solve our deconvolution task by minimizing the defect $\|S f - g\|^2$, then it leads to the following equation system $$S^T S f = S^T g \qquad (4.9)$$

In the left-hand side of (4.9) the matrix $S^T S$ is the autocorrelation matrix of the pulse, and it is positive semi-definite Toeplitz structured matrix. Thus, the left-hand side can be viewed as a convolution of the reflectivity with the pulse autocorrelation function. Let us denote $Q = S^T S$. In the right-hand side we clearly recognize match filtering of the RF-sequence by the pulse. Let us denote $b = S^T g$. So, the problem to be solved is $Q f = b$ and for obvious reasons it is ill posed. In order to achieve its stable solution we use the above-described approximate inverse approach. Note that in this case we seek for the inverse operator (filter) for the symmetric autocorrelation of the pulse.

As a suitable mollifier a low-pass filter with frequency response "surrounding" the pass-band pulse spectrum was chosen. The impulse response of such filter is the classical damped sinc-function. Thus, after the deconvolution (i.e., convolution with the inverse filter) we expect to obtain a low pass filtered version (moment) of the reflectivity function. In Figure No10 one can see the autocorrelation function of an estimated pulse and an approximate inverse filter appropriate to it.

Note the length of the inverse filter that is significant. The length depends on the spectral properties of the convolution kernel and the noise level. In the given case the kernel, i.e., ultrasound pulse, is narrow-band, consequently, in order to achieve an acute deconvolution, longer inverse filter should be used. The increasing the stabilization parameter of the inverse problem can reduce the filter length, but it is immediately expressed in weaker deconvolution.

In the next section these methods will be applied to RF-sequences measured *in vitro* from different tissue-mimicking phantoms.

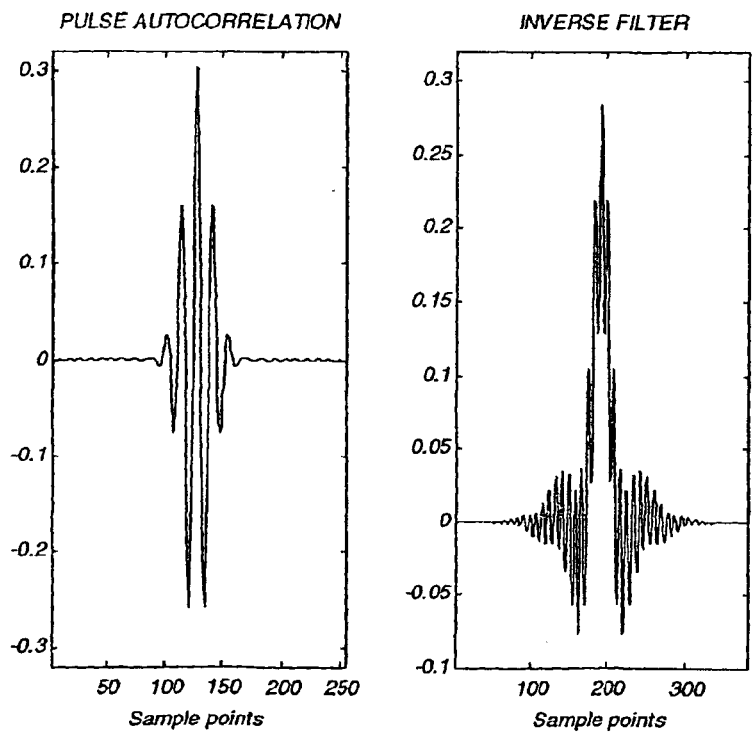

Figure No11: *Autocorrelation of the estimated ultrasound pulse and the approximate inverse filter appropriate to it*

5. EXPERIMENTAL RESULTS

Starting the experimental part of the work let us reminder the following assumptions on which based the proposed pulse estimation procedure.

- The ultrasound pulse is deterministic, possibly minimum phase
- The tissue response can be modeled as a stationary, white, zero-mean sequence, possibly Gaussian
- The additive experimental noise is taken from the Normal distribution with zero mean and variance $\sigma_u^2$, and it is statistically independent of the tissue response If we process a RF-line segment belonging to the speckled region of the interrogated tissue image, the above assumptions should hold. Outside such a region it is reasonable that the first and the third assumptions still exist, but the second could be violated. In order to avoid the estimate errors caused by the reflectivity function "coloration", it is possible to employ any segmentation procedure extracting from an entire RF-line those segments, which seems to be obtained from randomly distributed scatterers.

*Recordings*: 12 RF-lines were recorded from the tissue-mimicking phantom (Multipurpose Tissue/Cyst Ultrasound Phantom, 84-317, Nuclear Associates Prod.) using standard case type transducer (Panametrics V384 –SU) with central frequency of 3.5/0.25 MHz and the nominal focus zone of 4.515 inch. The transducer and the phantom were positioned inside a water tank, in such a way, that the target was located in vicinity of the focus. Each RF-sequence consisted of 512 sample points obtained from the same depth of, approximately, 4-cm. The sampling rate was chosen to be 50 MHz and the data acquisition was performed through the Tektronix-420 digital oscilloscope connected to a PC by a GPIB interface. Note that much lower rates are usually used for these purposes, but this choice is justified by a necessity to avoid possible aliasing errors in evaluation of the reflectivity function spectrum.

It was already pointed out, that the estimate errors are mainly caused by the non-whiteness of the reflectivity function. Distance-dependent attenuation of the RF-signal appears as a component, giving rise to the "coloration" of the reflectivity function spectrum. To eliminate its negative influence, the measured RF-sequences were divided into 2 shorter sequences of 256 sampling points each one. Note that this procedure is also necessary for providing the quasi-stationarity condition, assuming that inside of short enough RF-line segment the frequency-dependent attenuation does not distort the pulse spectral features strongly. Thus, the input data was structured in the form of two 256-by-12 matrices, which are appropriate to different (but adjacent) depths. The pulse estimation algorithm was applied to each column of these matrices, and subsequently, the obtained estimated pulses (12 for each data matrix) were averaged to obtain one pulse for each interrogated depth. Note that the averaging procedure can be implemented in the Wavelet domain or in the log-spectrum domain, and it is intended to decrease the estimate variance (assuming that the pulse in the adjacent lines is same). It has been observed that the estimated pulses obtained for the two data matrices (and so the appropriate averaged pulses) are not considerably different and it seems to be concentrated about a same mean value. It can be true, since it is reasonable to assume that the frequency-dependent attenuation process cannot appear significantly when comparing quite short (256 sample points) adjacent segments of the data. Analyzing the spectra of these sequences also shows that they constitute same statistical properties. For these reasons, we would not like to demonstrate the results of the pulse estimation separately for each depth, but it is of interest to compare the obtained estimation results with the ultrasound pulse measured in a water tank, when a thick planar perspex stick was used as a target. In the left-hand side of Figure No12 eight pulse estimates are viewed, whereas the right-hand side of this picture compares its average with the measured pulse.

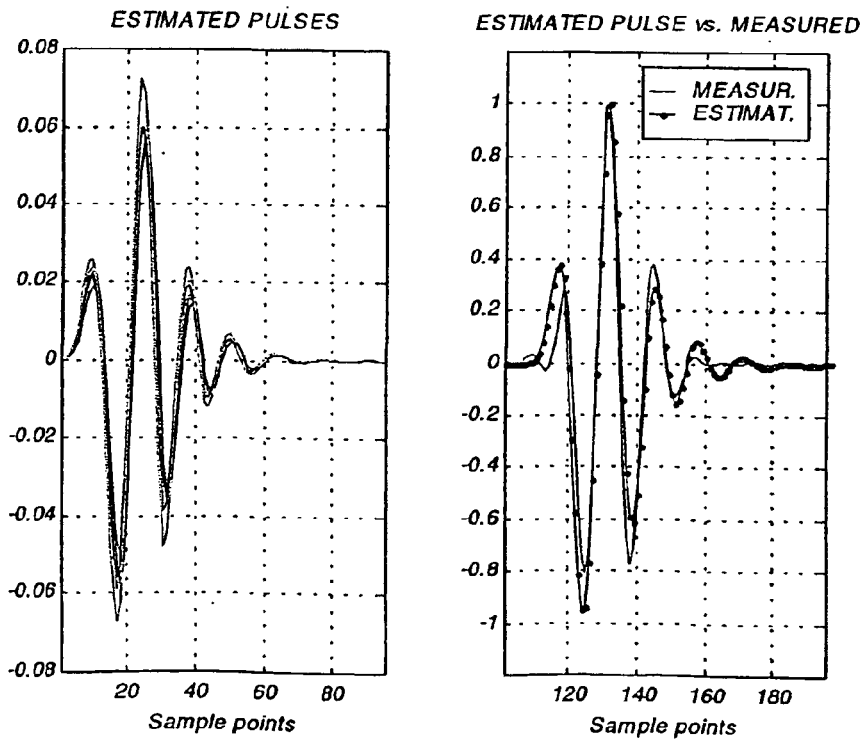

Figure No12: *Ultrasound pulse estimates from the data obtained using tissue mimicking phantom [left-hand side picture]; averaged pulse (dotted line) versus the measured pulse [right-hand side picture].*

It is obvious that there is a reasonable match between the average estimated and the measured pulses, but it is also obvious that in comparison with the measured pulse the estimated one seems to be "smeared", i.e. it has lower central frequency and wider time support. To verify this fact it is instructive to compare between the spectrums of the RF-sequence from which we estimate the spectrum of the pulse and the measured pulse spectrum.

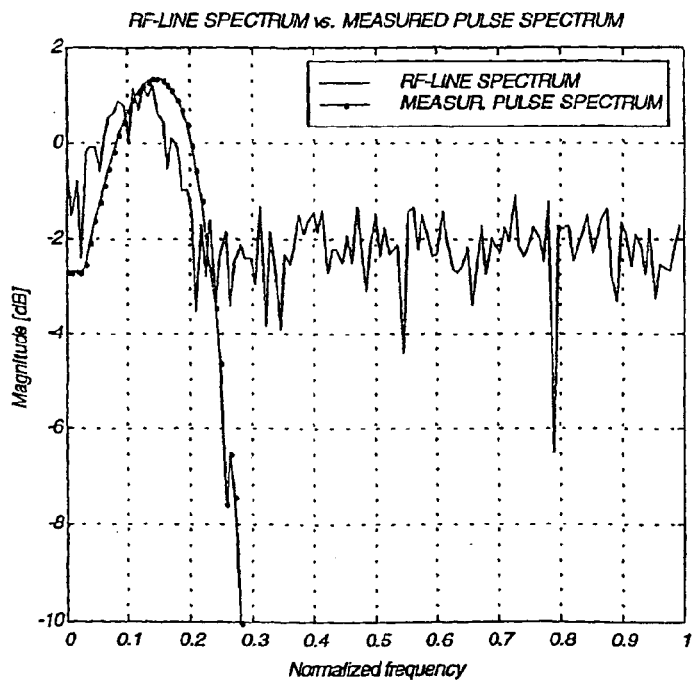

Figure No13: *Comparison between the RF-line spectrum and the spectrum of the pulse measured in a water tank from a planar reflector.*

In Figure No13 one can see the spectrum of one of the measured RF-line (recording from the tissue mimicking phantom) superimposed by the spectrum of the measured pulse (underwater recording from a thick planar perspex stick). Obviously, the central frequency of the former is biased toward lower frequencies and its "bell" seems to be a bit narrower in comparison with the latter. Thus, the "smearing" of the pulse estimate is reasonable and can be accounted for by the frequency-dependent attenuation processes existing in the phantom medium. Therefore, it leads us to the conclusion that the measured pulse does not truly represent the situation inside the issue-mimicking phantom.

Note that before the pulse estimation procedure, the input sequences were filtered using a low-pass filter in order to remove the out-of-band noise influence. In our specific case central frequencies of the interrogating pulse are quite remote from the lowest frequencies, thus another filtering is needed to cancel the noise distorting the beginning of the spectrum. Two standard LS designed filters were used for this purpose. The Wavelet decomposition up to level 4 was performed using standard Mallat Fast Wavelet transform algorithm with the wavelet filter from the "Coiflet" family (N=5). Note that another wavelets filter, such as minimum-phase wavelets of Daubechies (N=6,8), symmetric wavelets of Daubechies (N=6), some biorthogonal wavelets also demonstrated a good performance. The interrogating pulse was presumed to be minimum phase and its phase reconstruction was performed as described in Chapter 3.

Now given the estimated ultrasound pulse we can construct an appropriate inverse filter and check its deconvolution performance. To construct the inverse filter we have to choose a suitable mollifier, as it was described in Chapter 4. This choice depends mainly on the pulse spectrum and in the given case the scaling function constructed by Meyer (available in the Matlab toolbox through the routine "wavefun"), was chosen for these purposes. In the Fourier domain it constitutes a low-pass filter with a smooth, continuous cut-off slope [12], that allows the *effective* support of the function in the time domain to be quite local (but generally speaking, the support of such a filter is infinite). Note that using the ideal low-pass filter is never a good choice (despite it might seem reasonable from the spectral point of view), since its impulse response extends to the infinity. Thus, by choosing a differentiable spectrum (i.e., allowing the continuity in its cut-off region) it is possible to decrease significantly the negative effects of infinite filter lengths. Another choice of the mollifier is also possible, and it is fairly a matter of opinion [10].

An additional difficulty encountered in the process of the inverse filter construction is caused by the ultrasound pulse spectral properties. The used pulse was quite narrow band, and consequently the inverse filter is not able to "whiten" its spectrum perfectly (within the limits dictated by the mollifier pass-band). This situation is depicted in Figure No14, on the left-hand side of which one can see the inverse filter computed for the estimated pulse, and the right-hand side shows the result of its convolution with the pulse itself. It should be noted here, that the inverse filter was computed for the pulse, in place of its autocorrelation sequence, as it was described in Chapter 4, and only insignificant correction is needed to do it. Regarding the deconvolution results, we clearly see that the deconvolved result resembles the typical low-pass filter impulse-response, but its side ripples are obviously larger in comparison with the latter. This artifact is fairly ascribed to the difficulty of the inversion of narrow-band spectra, and it may introduce an inaccuracy in the tissue response moment (low-frequency components) evaluation, and the latter appears as a weaker deconvolution. Yet, fortunately, in our specific case the resulted kernel is close enough to be a low-pass filter impulse response, and no considerable errors are expected.

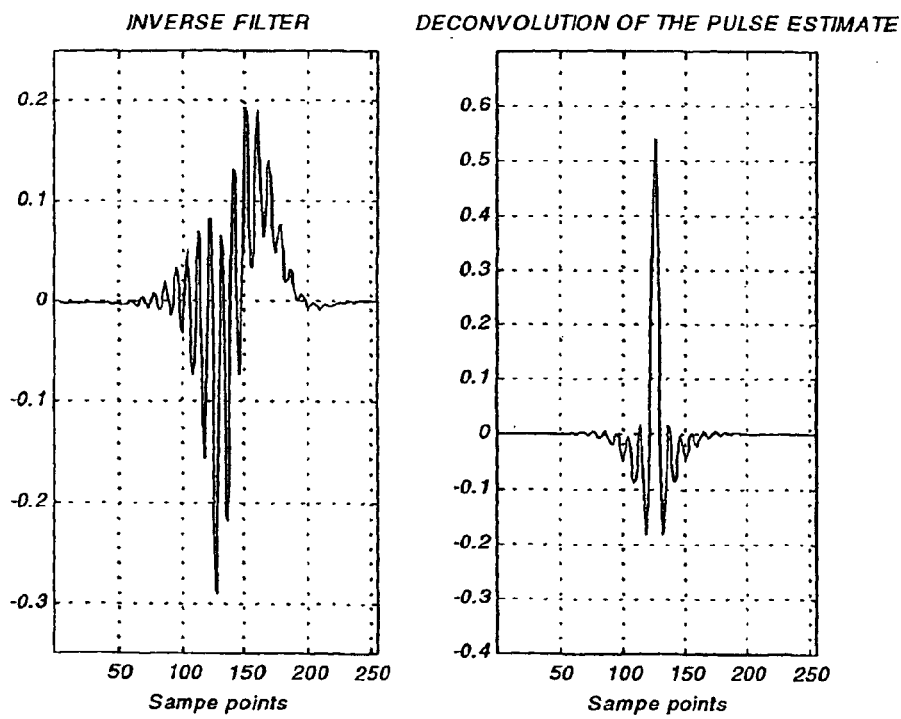

Figure No14: Inverse filter computed for the average estimated pulse (note, that it is not a filter for the pulse autocorrelation sequence, as it was shown in Chapter 4, but

*for the pulse itself) [left-hand side]; result of the deconvolution of the estimated pulse by the inverse filter [right-hand side].*

In despite of above-mentioned difficulties, it is now clear that the deconvolution of the RF-sequences should results in a significant reduction of the time-spatial support of the interrogating pulse, suggesting an apparent gain in the axial resolution. Therefore, we hope that the deconvolved RF-lines will resemble low-pass filtered versions of the appropriate tissue response sequences, and it will supply us more valid information about the scatterers' location and distribution.

In order to investigate to performance of our technique, we applied the deconvolution procedure to the RF-sequences obtained form the same earlier used tissue-mimicking phantom. Starting the analysis of the obtained results we have to emphasize, that due to the finite size of the beam the received RF-sequences are not combined from echoes from the scatterers and reflectors located exclusively on a line that is an axial symmetric axis of the transducer. A RF-line gets benefits from the scatterers and reflectors located in the entire 3-D region of the insonified tissue defined by the beam thickness in the focus. Since our algorithm does not treat the lateral resolution, after the deconvolution procedure we cannot identify form which regions exactly (within the limits of the ultrasound beam) the reflections were obtained. This fact disturbs us to check validity of the algorithm performance in experiments with the tissue-mimicking phantom.

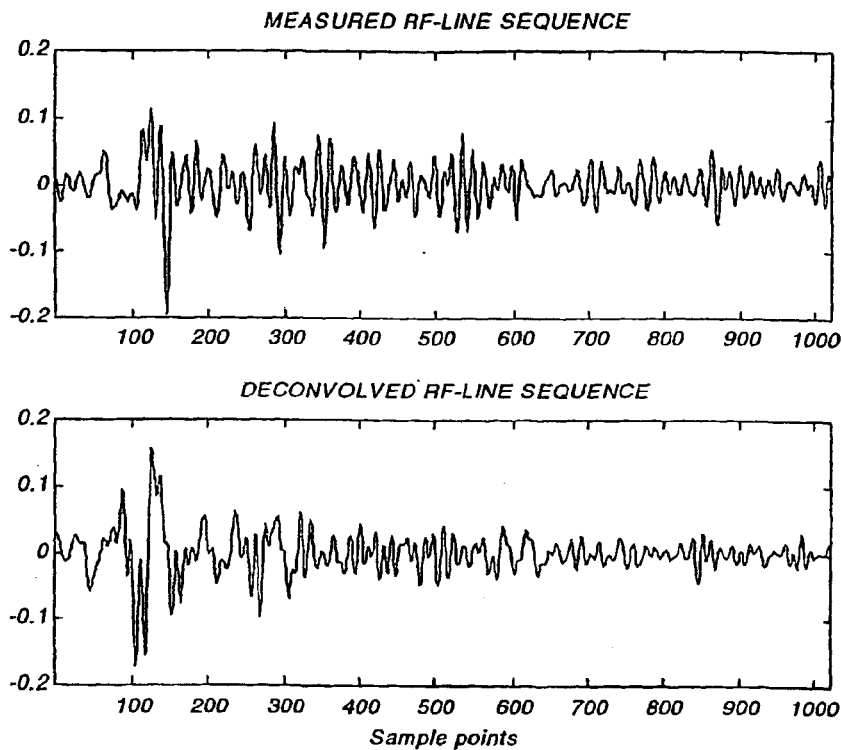

Figure No15: Measured RF-sequence [upper picture]; the same data after the deconvolution [lower picture].

Figure N15 (upper picture) shows the RF-sequence received from the tissue-mimicking phantom and filtered by an appropriate band-pass filter, whereas the lower picture demonstrates the same RF-line after applying the deconvolution procedure to it. Note that the insonified region had no strong reflectors, therefore, it is reasonable that this RF-line might contribute to a speckled region of an image. At the first glance, the differences between the sequences are not so obvious, but an analysis of its spectra shows that the deconvolved RF-line spectrum has been whitened, i.e., it is almost flat in the frequency interval up to the cut-off frequency of the noise canceling filter. Thus it leads us to the conclusion that the obtained signal has the same statistical properties, which were assumed for the reflectivity function in the speckle region. Unfortunately, it is not possible to prove whether the deconvolved sequence indeed constitutes the low-pass filtered version of the original tissue response.

The idea to prove the validity of the scatterers' identification brought us to usage of a phantom specially constructed for this purpose. There are two principal features, which must be provided in construction of such a phantom. First, it should be combined of parallel layers jointed together having a lateral size much larger in comparison with the beam thickness. In such a case, we can ignore the artifacts contributed by non-treatment of the lateral resolution, and one can say that the reflectivity function is now reasonably one dimensional, and all its scatterers are arranged along this dimension. Second, the distances between the layers and its widths should be random (possibly taken from the normal distribution). It also should be chosen to be smaller in comparison to the wavelength in order to supply us RF-lines with significant echo interference.

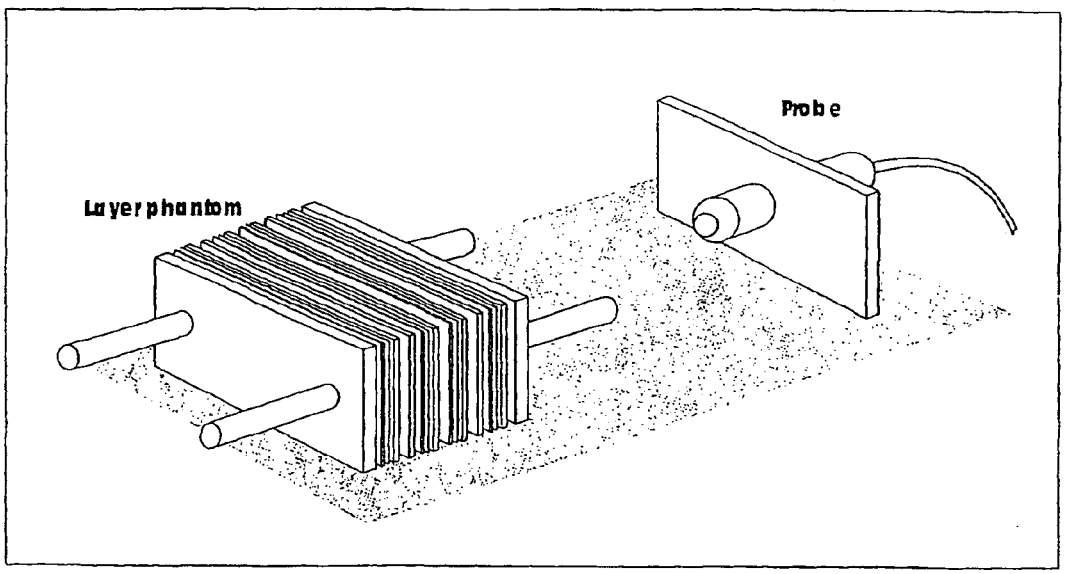

Figure No16: *Specially constructed phantom consisting of perspex and plastic layers with random widths and distances between them.*

This phantom is viewed in Figure No16. It was constructed form several plastic and perspex sheets having different widths and jointed together in such a way that the distances between the sheets are random with a good precision. Despite of our attempts, for obvious reasons we could not find plastics with depths taken from the normal distribution, and thus, only plastics with $\Delta$= 0.44, 0.5, 0.8, 0.9, 1.2, 1.44, 1.5, 1.8 mm were randomly mixed and attached one to the another. Clearly, there is one serious problem with such a phantom structure. Since the phantom is intended for underwater experiments, the pulse propagating through it, always passes sequentially from a more dense to a less dense, and subsequently, from a less dense to a more dense matter (i.e., from the plastic to the water and vise versa). It other words the odd samples of the reflectivity sequence may be, for example, positive, whereas all the even samples are negative. It implies that these samples are highly correlative, and it appears as a "coloration" of the spectrum. It was already pointed out that such deviation from the whiteness could introduce inaccuracy in the pulse estimation. Yet, fortunately, in process of the experimentation we observed that errors caused by this problem are not crucial.

Clearly that this phantom is far to be physical, but let's reminder that it was created especially to check an axial resolution gain after deconvolution. The pulse-estimating algorithm was applied to the RF-sequences received from the phantom. It is reasonable to expect that overall character of the pulse inside this specific phantom should not be too unlike the pulse measured from a planar reflector orthogonal to the beam in the water tank. Thus, the capability of the algorithm to estimate pulses will be investigated by comparison of the estimated pulses with results of the measurements. The results of the estimation already have been shown in Figure No10 of Chapter 3. In the right-hand side of the picture the average estimated pulse is compared with the pulse measured in a water tank. Correspondence between the estimated and the measured pulses is striking.

The estimated pulse was used to compute the inverse filter. This procedure is absolutely analogous to one described earlier, and the inverse filter obtained in this case is negligibly different from the filter viewed in Figure No14 (right-hand side). The results of the deconvolution are depicted in Figure No17, where the upper picture demonstrates a fragment of the measured RF-line, whereas the lower picture demonstrates a sequence obtained after applying the inverse filter to the former. The dashed line on both pictures is an envelope of the original RF-line, and it allows the visual comparison of the deconvolved sequence with the conventionally processed sequence (dashed line). Visual comparison of the two plots makes additional explanations redundant. Obviously, after the deconvolution we can easily distinct between the echoes reflected from surfaces of the phantom layers. Comparing it with the RF-envelope (dashed line), we conclude that significant axial resolution enhancement is possible with deconvolution.

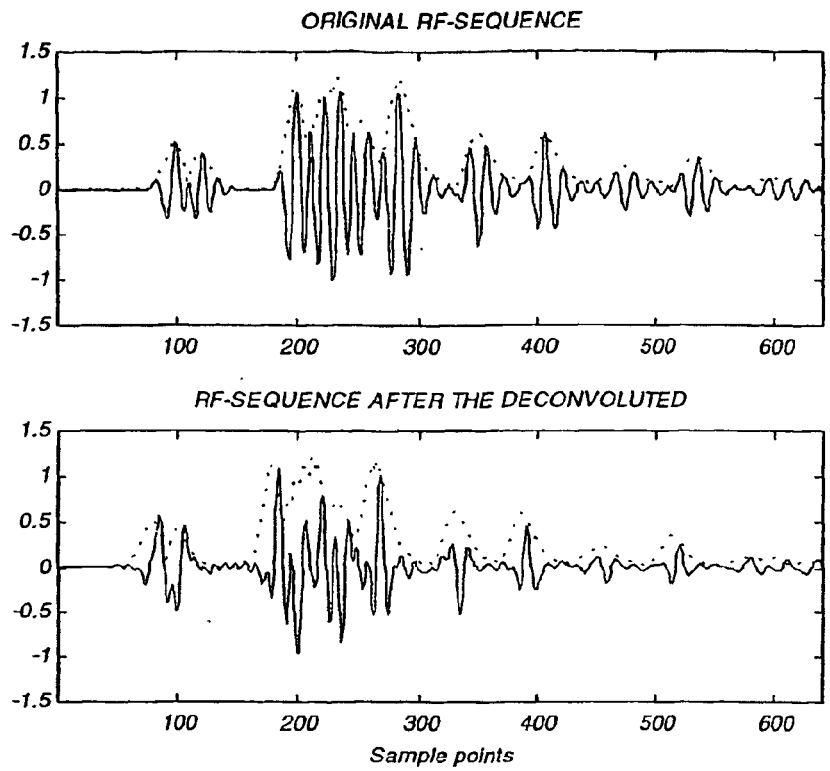

Figure No17: *RF-line measured from the phantom consisting of plastic layers [upper picture]; result of the deconvolution of this sequence [lower picture]. Note that the dashed line on both pictures is an envelope of the original RF-line*

6. CONCLUSIONS

This paper has demonstrated a novel pulse estimation technique based on the homomorphic signal processing and the Wavelet analysis of the log spectra. The proposed method is close in concept to the well-known cepstrum-based methods [1], [2], [4-6], but there are also several conceptual differences, which makes the algorithm quite attractive. The procedure is implemented in the log Fourier domain allowing to avoid some artifacts related to the cepstrum computation (aliasing error, for example). It was observed that the algorithm is quite tolerative to experimental noises, and its performance is quick enough (possibility of using in the real time) due to efficient scheme, known as Fast Wavelet transform, discovered by Mallat [14].

It was emphasized that not all the wavelet filters give identical results, and best performance is achieved with long, regular wavelets. This technique was applied to *in vivo* experimental data obtained from the different tissue mimicking phantoms, and it was shown that our pulse estimation procedure could be done with reasonable accuracy. The accuracy of the estimation was verified by underwater measuring the ultrasound pulse from a thick planar reflector orthogonal to the beam. There is a reduction in the variance of the estimate, when several estimated pulses are averaged.

In order to reconstruct phase of the pulses, minimum phase assumption was made. Generally speaking, the interrogating ultrasound pulse might not be minimum phase, but it was experimentally shown that the pulses used in the given case satisfy this condition with good precision. Currently, the topic of generalization of the algorithm for the non-minimum phase conditions is an object of our intensive attention.

The estimated pulse was used in order to construct the approximate inverse filter employed for deconvolution purposes. Deconvolution results obtained with the tissue-mimicking phantom data and, in most degree, with the specially constructed "layers-build" phantom data indicate considerable axial resolution improvement. It has been reported that wide-band pulses are preferable for achieving better deconvolution results.

Due to the apparent gain in the axial resolution after the deconvolution those small structures (early stage tumor, for example) that are hidden away from view should be revealed. In addition to it, it was shown that a successively deconvolved sequence should constitute a moment (low-pass filtered version) of the "true" reflectivity sequence (tissue response), that is largely independent of the imaging system. As a consequence of the fact, these sequences might be used for tissue characterization schemes, which ideally require the above-mentioned independence. It can be added that appropriate analysis of the pulse shape estimated from different depths of the interrogating tissue also could carry a useful information about the frequency deponent attenuation processes.

In conclusion, this paper establishes the 1-D deconvolution as a powerful technique removing the image distortion in the axial direction. Despite of the fact that such a procedure does not treat the "smearing" of images in the lateral direction, there are diverse kinds of applications where it could be very useful.

7. ACKNOWLEDGMENT

We are very grateful to Zvi Fridman for providing the tissue mimicking phantom and his valuable suggestions, to Dan Bodik for constructing the "layers-built" phantom. We wish to thank the anonymous reviewers whose comments substantially improved the paper.

REFERENCES

[1] Udantha R. Abeyratne, Athina P. Petropulu, Jonh M. Reid, "Higher order spectra based deconvolution of ultrasound images", *IEEE Transactions on Ultrasonics, Ferroelectrics and Frequency Control*, vol. 42, no. 6, November 1995

[2] Torfinn Taxt, "Restoration of medical ultrasound images using two-dimensional homomorphic deconvolution", *IEEE Transactions on Ultrasonics, Ferroelectrics and Frequency Control*, vol. 42, no. 4, July 1995

[3] Kjetil F. Kaaresen and Erik Bolviken, "Blind deconvolution of ultrasonic traces accounting for pulse variance", *IEEE Transactions on Ultrasonics, Ferroelectrics and Frequency Control*, vol. 46, no. 3, May 1999

[4] Torfinn Taxt, "Comparison of cepstrum-based methods for radial blind deconvolution of ultrasound images", *IEEE Transactions on Ultrasonics, Ferroelectrics and Frequency Control*, vol. 44, no. 3, May 1997

[5] J. A. Jensen and S. Leeman, "Nonparametric estimation of ultrasound pulses", *IEEE Transactions on Biomedical Engineering, vol. 41, pp. 929-936, 1994*

[6] J. A. Jensen, "Deconvolution of ultrasound images", *Ultrasonic Imaging, vol. 14, pp. 1-15, 1992*

[7] A. V. Oppenheim and R. W. Schafer, *Discrete time signal processing*, London: Prentice Hall, 1989

[8]  D. G. Childers, D. P. Skinner and R. C. Kemmerait, "The cepstrum: A guide to processing", *Processing IEEE, vol. 65, pp. 1428-1443, 1977*

[9]  T. J. Ulrych, "Application of homomorphic deconvolution to seismology", *Geophysics, vol. 36, pp. 650-660, 1971*

[10]  A. K. Louis, "Approximate inverse for linear and some nonlinear problems", *available from http://www.num.uni-sb.de/gebiete/invers/e_approx.html*

[11]  "Mathematical model for the ultrasound pulse sequence"

[12]  I. Daubechies, "Different Perspectives on Wavelets", *American Mathematical Society, Short Course, January 11-12, 1993*

[13]  Stephane G. Mallat, "Multifrequency channel decomposition of images and Wavelet models", *IEEE Transactions on Acoustic, Speech and Signal Processing, vol. 37, no. 12, May 1989*

[14]  Stephane G. Mallat, "A theory for multiresolution signal decomposition: The Wavelet representation", *IEEE Trans. Pattern. Anal. Mach. Intell. 11, 1989, pp. 674-693*

[15]  E. Sekko, G. Thomas, A. Boukrouche, "A deconvolution technique using optimal Wiener filtering and regularization", *Signal processing, 72, pp. 23-32, 1999*

[16]  Per Christian Hansen, "Numerical aspects of Deconvolution", *available from http://www.imm.tdu.dk/~pch*

ANNEX B

ROBUST ULTRASOUND PULSE SPECTRUM ESTIMATION ALGORITHM USING OUTLIER RESISTANT DE-NOISING

Dan Adam and Oleg Michailovich

1. SPECKLE NOISE

Due to coherence of the back-scattered echo signals, images obtained from echo ultrasound imaging systems have extremely complex pattern bearing no obvious relationship to the macroscopic properties of the insonified object. The vast majority of biological tissues are extremely rough on the scale of an acoustical wavelength, and consequently a signal obtained within a resolution cell consists of contributions of many independent scatterers. Interference of these de-phased echoes gives rise to pattern, which has appearance of a chaotic jumble of "speckles", known as speckle noise. The speckle pattern consists of a multitude of bright spots where the interference has been highly constructive, dark spots where the interference has been highly destructive, and brightness levels between these extremes. It appears chaotic and unordered, and it might be described quantitatively by methods of probability and statistics. The presence of speckle in an image reduces the ability of a human observer to resolve fine details. It obscures very small structures (early stage tumor, for example) decreasing reliability of tissue characterization. Thus in most cases of practical interest, suppression of the speckle noise is a goal towards which we aspire.

2. BASIC MODEL

One approach of describing the scattering of tissue is to consider the acoustic inhomogeneity as an assembly of reflectors and scatterers. The former is a plane interface large, compared to the wavelength, reflecting portions of the transmitted energy back toward the transmitter. The latter is a small object, compared to the wavelength, spreading the transmitted signal in all directions, reflecting small portions of the energy. It is acceptable to model such a system by a (generally speaking three-dimensional) function called the spatial response of insonified material, or in the case of medical imaging spatial tissue response or reflectivity function. Below it will be referred to as the reflectivity function.

One can consider an ultrasound radio frequency image (RF-image) as combined of 1-D echo-sequences, or using the terminology of the ultrasound community, RF-lines. Assuming the tissue properties to be uniform in the plane perpendicular to the scanning beam, one can view an obtained 2-D RF-image as result of the convolution of the 2-D reflectivity function (which accounts for inhomogeneity in the scanning plane) and 2-D transducer point spread function (PSF). Thus, the RF-image can be considered to be a distorted version of the true reflectivity function, where the distorting kernel is the transducer PSF. Its influence results in deforming the useful information about a tissue (appearance of the speckle noise). The speckle noise affects the quality of ultrasonic images in which it is present by reducing the contrast, lowering the signal to noise ratio (SNR) and obscuring important diagnostic details. So the task of recovering of the reflectivity function from the received signal is of great importance. Unfortunately, this problem is more complicate, since the system PSF cannot be considered to be available. The absorption of the ultrasound energy in tissues increases with frequency. This frequency-dependent attenuation process causes to both the pulse amplitude and shape to be dependent on depth in tissue and leads to the observed non-stationarity of RF-sequences.

3. ONE-DIMENSIONAL APPROACH

In medical ultrasound, a pulsed field is transmitted into the body, and the echoes, back scattered toward the emitting transducer, are detected as a voltage trace, RF-line. It has proved fruitful to model the RF-line directly as being result of combining a hypothetical 1-D pulse with a hypothetical 1-D tissue. Assuming scatterers on each image line be located on a uniform grid and the system impulse response is range shift invariant along each image line, the beam former gives a single receive signal equal to the coherent sum of the echoes only from on grid scatterers. A discretized version of this receive signal can be written as $$rf(t) = \sum_{k=1}^{N} a_k s(t-k) + n(t) \qquad (1.1)$$

Here $rf(t)$ is RF-line, $s(n)$ is the transmitted ultrasound pulse, $k$ is twice the time-of-flight to the $k-th$ reflector, and $n(t)$ is measurement noise. Note that it is assumed here that the reflectors themselves do not modify the pulse except by a real scaling factor $a_k$. Using the convolution notation one can rewrite (1) as follows.

$$rf[n] = a[n] * s[n] + noise[n] \qquad (1.2)$$

Here $n$ may be referred to as a time index, and $a[n]$ is a reflectivity sequence. Since the frequency-dependent attenuation process appears as decrease with distance of the mean frequency and the amplitude of the pulse, it is commonly assumed that the received pulse-echo signal may be expressed as a depth dependent pulse convoluted with tissue reflectivity function. Therefore, in (1.2) the pulse is to be "location-dependent" (i.e. $s[n]$ must be replaced by $s[n, k]$, where $k$ is the location index), and it leads to the observed non-stationarity of the RF-lines received from the tissue. In order to deal with the non-stationarity it was proved to be fruitful to break up the RF-sequence into a number of possibly overlapping segments. In such a case it is reasonable to state that within each segment the frequency-dependent attenuation process does not affect the pulse spectrum properties considerably and the equation (1.2) holds. So, the problem of the reflectivity function derivation or, the same, the problem of tissue characterization can be reformulated in term of the blind deconvolution problem, namely, for each segment of a given RF-line the ultrasonic pulse should be estimated and "extracted" from it. A problem that could arise in such approach is that short data intervals might not contain enough data for precise estimation. The pulse estimation method proposed in this paper is tolerative enough to this "data insufficiency" problem, and thus, the above-mentioned "segment-wise" processing will be used throughout this paper. Additionally we note that a successively deconvolved RF-sequence should constitute a moment (low-pass filtered version) of the "true" reflectivity sequence, that is largely independent of the imaging system. Consequently, these sequences might be used for tissue characterization schemes, which ideally require the above-mentioned independence. In addition to it, due to the apparent gain in the axial resolution after the deconvolution those very small structures (early stage tumor, for example), that are hidden away from view, should be revealed.

4. HOMOMORPHIC ANALYSIS AND SPECTRAL SEPARATION

We start the algorithm derivation assuming that a received RF-line was segmented, and that a chosen segment to be deconvolved is modeled by (2.1). This equation can be specified in the frequency domain by taking the Fourier transform on both its sides.

$$RF(w) = A(w)S(w) \qquad (2.1)$$

Note that in (2.1) for the sake of simplicity we temporarily ignore the noise term. Of interest here is the fact that the RF-line spectrum is obtained as a result of multiplying the pulse spectrum by the reflectivity function spectrum and they are quite different from the viewpoint of its spectral features. One of the most acceptable models for the ultrasonic pulse sequence is such in which it is defined as a smooth Gaussian-like function modulated by an exponential of certain phase. It implies that the pulse spectrum should be a smooth, "slow" function with a maximum in vicinity of the nominal resonance frequency of the transducer. Such a spectrum cannot admit considerable ruptures or spikiness. In Figure No1 one can see the filtered pulse-echo signal received from a planar reflector in a water tank and its DFT (Discrete Fourier Transform). Assuming that the reflectivity function of this elementary reflector is a zero sequence with only one weighted digital delta appearing at the point appropriate to the "two-flight" time, the echo signal is to be close to our pulse.

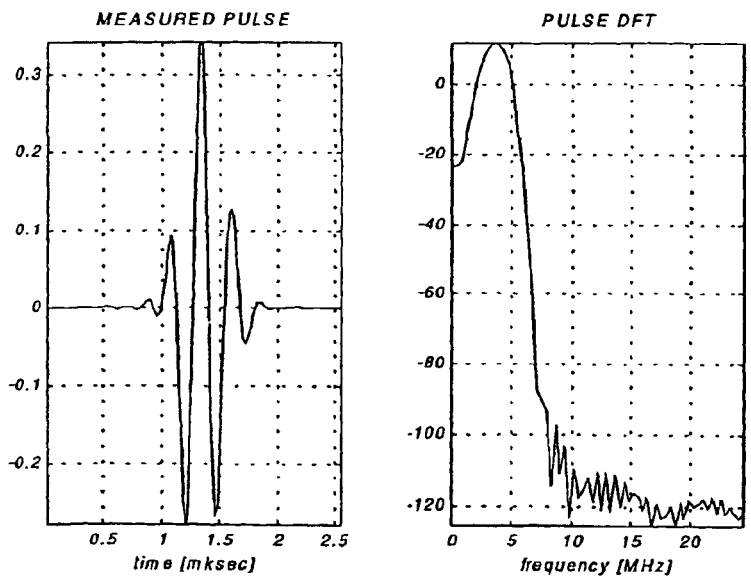

Figure No1: *(left-hand figure) ultrasonic pulse measured from a planar reflector in a water tank; (right-hand figure) DFT of the pulse*

It is well understood that the reflectivity function ascribed to speckled regions (soft tissue) of ultrasound images may be modeled as a random process combined of independent identically distributed random variables exhibiting complexity of the underlying tissue structure. Such reflectivity sequences will have very irregular, spiky DFT with numerous ruptures and dips. Moreover such a spectrum should be broadband in contrast to the pulse spectrum. Hence the RF-sequence DFT is nothing more than a result of the multiplication of the irregular, "wild", broadband reflectivity function DFT by the smooth and band-limit DFT of the ultrasonic pulse. In Figure No2 one can see a simulated periodogram of the reflectivity function and a typical spectrum of the measured RF-sequence taken in logarithmic scale.

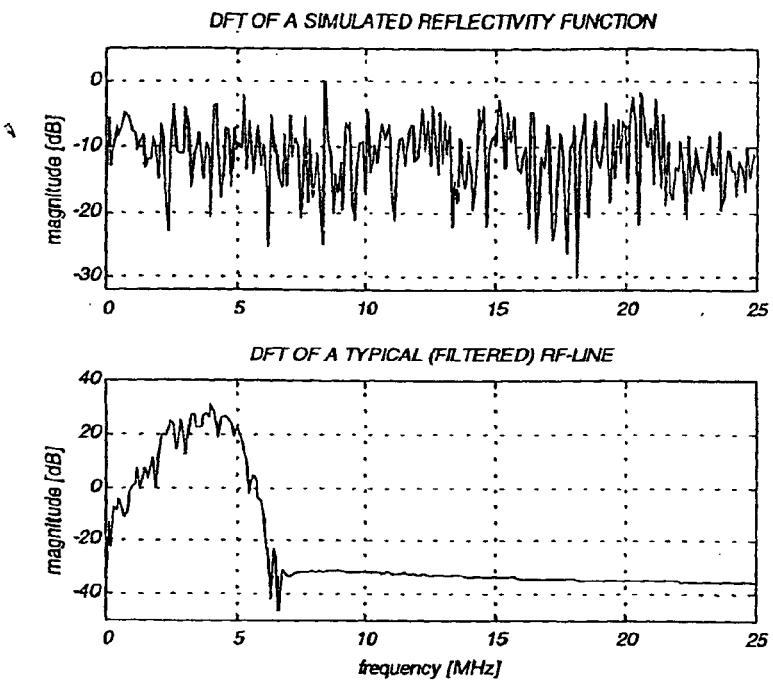

Figure N2: *(upper figure) DFT of a simulated reflectivity function; (lower figure) DFT of a typical filtered RF-line obtained from a soft tissue*

Now, let us consider the complex logarithm of the $RF(w)$ in (2.1). The Fourier transform of the RF-sequence can be defined in terms of its amplitude and argument $RF(w) = |RF(w)| \cdot e^{j \cdot \arg(RF(w))}$. Similarly, define $S(w) = |S(w)| \cdot e^{j \cdot \arg(S(w))}$ and $A(w) = |A(w)| \cdot e^{j \cdot \arg(A(w))}$. As a result, the following, well known in the homomorphic signal processing relationships can be obtained.

$$\log\{|RF(w)|\} = \log\{|S(w)|\} + \log\{|A(w)|\}$$
$$\arg[RF(w)] = \arg[S(w)] + \arg[A(w)] \quad (2.2)$$

We see that the log-amplitude of the $RF(w)$ can be represented as a sum of two components, namely, the smooth and regular log-spectrum of the ultrasonic pulse and very jagged and irregular log-spectrum of the reflectivity function. If we glance at these functions from the point of its scales, it will be clear that $\log\{|S(w)|\}$ is much "slower", than $\log\{|A(w)|\}$ and it implies that its scales are quite different. Hence, it is reasonable to assume that its frequency spectra (i.e., frequency spectra of the log-spectra) do not overlap significantly and one can separate the two components. One approach for recovering the log-spectrum of the pulse is based on the following fact. From the multiresolution analysis point of view, the pulse log-spectrum can be considered as a signal belonging to the subspace of the lower resolution, while the reflectivity function log-spectrum is a signal which belong to the space of higher resolution. Therefore in order to recover the former all we need is to project the RF log-spectrum in an appropriate space. In order to implement the above-mentioned projection, the Wavelet transform is used. Adjusting the resolution level one can obtain an approximation of the analyzed signal, which in the given case, is a good estimate of the pulse log-spectrum. Clearly the pulse estimate itself can be obtained inverting the previous steps.

The above "projection" method is very fast and efficient. Technically it requires only wavelet decomposition of $\log\{|RF(w)|\}$ supplying us a vector of the wavelet coefficients, following by the linear shrinkage (i.e., setting to zero) all the coefficients up to a prescribed level. Obviously, it is assumed that these shrunken (i.e., zeroed) coefficients bear bulk of the energy associated with the log-spectrum of the reflectivity function. After the linear shrinkage an estimate of the pulse log-spectrum is obtained by the inverse transformation. Despite its attractiveness this method demonstrates some inconvenience in optimal choices of the decomposing filter and the decomposition level. Indeed, non-optimal choice of the level up to which the wavelet coefficients are to be shrunken may cause a sneaking of wavelet coefficients induced by the "reflectivity" part of $\log\{|RF(w)|\}$ in the pulse log-spectrum estimate.

Obviously, it might influence destructively the estimate quality. On the other hand, if such a level were chosen "deep" enough, we would expunge some coefficients whose significance in the estimate is crucial. Moreover, the separability of the spectra in the Wavelet domain essentially depends on the filter smoothness. Nevertheless, these algorithm parameters (i.e., the decomposition "depth" and the filter regularity) can be optimized, and the method demonstrates quite acceptable results.

In the paper, another approach for recovering the pulse log-spectrum will be proposed. This method is non-parametric and much more robust. It considers $\log\{|RF(w)|\}$ as being combined from a signal to be recovered, i.e. the pulse log-spectrum and noise, which in the given case is the log-spectrum of the reflectivity function. Thus, in order to recover the log-spectrum of the pulse we have to "filter out" the irregular jagged components ascribed to the latter. The procedure of recovering a desired signal from its measurements contaminated by noise using non-linear shrinkage of its wavelet coefficients is known as *de-noising*. In order to implement it we will use the algorithm, which was proposed by David L. Donoho and Iain M. Johnstone in 1992. Note that in series of latter papers, the authors significantly modernized their initial idea by proposing the adaptive de-noising (1993), ideal de-noising in a best basis chosen from a library of bases (1994), translation-invariant de-noising (in collaboration with Ronald R. Coifman, 1995). These algorithms are consistent and progressive developments of the first work, and each work is a logical continuation of the previous one. For the reason of the space we don't test here performance of the pulse estimation using all these excellent de-noising methods, and only the first (i.e., initially proposed) algorithm will be used in the paper.

5. PROJECTION METHOD

We start by describing the earlier proposed method for recovering the pulse log-spectrum. In base of the algorithm is the property of the Wavelet transform that causes the decomposition of a polynomial to produce null details, when the number of vanishing moments of the wavelet exceeds the degree of the polynomial. Now we would like to cite the following theorem proved by I. Daubechies that is of great importance for our discussion.

<u>Theorem1</u>: If $\psi_{m,n}(t) = 2^{-m/2}\psi(2^{-m}t - n)$ constitute an orthonormal set in $L^2(\Re)$ with $|\psi(t)| \leq C \cdot (1+|t|)^{-K-1-\varepsilon}$, $\psi(t) \in C^K(\Re)$ and $\partial^k \psi / \partial t^k$ is bounded for all $k \leq K$, then $$\int dt \cdot t^k \cdot \psi(t) = 0, \quad \text{for } k = 0, 1, \ldots, K \qquad (3.1)$$

From the above theorem stems that if analyzed signal is polynomial with degree less that $K$, then its wavelet coefficients are zero for all $n,m$. It says that wavelets automatically suppress the polynomials. Let us suppose that on the interval $[a,b]$ including $0$, we have expansion of the signal $x(t)$ $$x(t) = x(0) + x \cdot \frac{\partial x(0)}{\partial t} + x^2 \cdot \frac{\partial^2 x(0)}{\partial t^2} + \ldots + x^K \cdot \frac{\partial^K x(0)}{\partial t^K} + y(t) \quad (3.2)$$

In (3.2) the signal $y(t)$ is the irregular part of the signal $x(t)$. According the Theorem1, the signals $x(t)$ and $y(t)$ have the same wavelet coefficients. In other words, the $\psi$ wavelet suppresses the regular, polynomial part of $x(t)$ and analyses the irregular part.

From the discussion of the previous section, the pulse log-spectrum is quite smooth signal, which can be considered as a polynomial of certain degree. Thus it is reasonable to expect that if the number of the vanishing moments of chosen wavelet exceeds the polynomial degree, then its wavelet coefficients will be equal to zero. On the other hand, the reflectivity function log-spectrum is quite irregular, noisy signal, which cannot be considered to be polynomial (at least, polynomial with degree less than the vanishing moments number of the most wavelets in use), thus its wavelets coefficient are never zero. Consequently, the log-spectrum of RF-line can be considered combined from the regular part (i.e., the pulse log-spectrum) and the irregular part (i.e., the reflectivity function log-spectrum). Thus, if the analyzing wavelet is chosen to have number of the vanishing moments exceeding the polynomial order, then the wavelet coefficients are fairly associated with the reflectivity function log-spectrum, i.e. the wavelet suppresses the "slow" pulse log-spectrum which is locally assimilated to a polynomial.

Now let us describe the algorithm implementation from the practical point of view. We define a family of DWT indexed by two integer parameters $L$ and $M$. Strictly speaking, regarding implementational particularities we also have to define a kind of the transformation, either "periodic" or "boundary adjusted". For a fixed value of $L$ and $M$ we get a matrix $W$. Multiplication of data vector $\{y_i\}_{i=0}^{n-1}$, $n = 2^J$, by this matrix gives the *wavelet coefficients* of $y$.

$$w = W \cdot y \qquad (3.3)$$

It must be emphasized that in practice the DWT is not implemented by matrix multiplication, but by a sequence of finite-length filtering followed by a decimation step. The choice of the Wavelet transform is essentially a choice of filter. In the orthogonal case (which we choose for simplicity in exposition) we have the inversion formula $$y = W^T \cdot w \qquad (3.4)$$

Let $w_{j,k}$ denote the wavelet coefficients indexed dyadically, such that $j = 0,\ldots,J-1$, $k = 0,\ldots,2^J - 1$ and $W_{j,k}$ denote $(j,k)-th$ row of $W$. Then the inversion formula (3.4) can be rewritten as $$y = \sum_{j,k} w_{j,k} \cdot W_{j,k}(i) \qquad (3.5)$$

One can see that the data vector $y$ can be represented as the above linear combination of the basis element $W_{j,k}$ with coefficients $w_{j,k}$.

For $L < j \ll n$, $0 \ll k \ll 2^J$ we have the approximation $$\sqrt{n} \cdot W_{j,k}(i) \approx 2^{j/2} \cdot \psi(2^j t), \quad t = i/n - k \cdot 2^{-j} \qquad (3.6)$$

Here $\psi$ is the *mother wavelet* arising in a Wavelet transformation on $\mathfrak{R}$, as described in Daubechies (1988,1992). She has shown that the parameter $M$ controls the smoothness (number of the vanishing moments) of $\psi$. The greater the $M$, the smoother the mother wavelet.

Practically it is usual to perform the DWT (Discrete Wavelet Transform) using the classical Fast Wavelet Transform (FWT) algorithm of Stephan G. Mallat using the filter-bank technique. This adapts to the present situation as follows. Let us denote an approximation of the data signal at resolution level $j = L$ by $V_L y$ and *details* of the signal at resolution level $j$, or scale $2^{-j}$ by $W_j y$. It is given by $$V_L y = \sum_{j<L} w_{j,k} \cdot W_{j,k} \qquad W_j y = \sum_{0 \le k 2^j} w_{j,k} \cdot W_{j,k} \qquad (3.7)$$

Then $y$ can be recovered from these components via $$y = V_L y + \sum_{L \le j < n} W_j y \qquad (3.8)$$

Now suppose that a given RF-line log-spectrum was decomposed according to (3.8). If parameter $M$ of the DWT was chosen sufficiently large, then the second term of (3.8) bears an information related exclusively to the reflectivity function log-spectrum. Thus, reconstruction from the only first term of (3.8), which is reasonably connected to the polynomial part of the signal under consideration and constructed from the wavelet coefficients induced by the pulse log-spectrum will give us an acceptable estimate of the latter. It is clear, that the choice of the second decomposition parameter $L$ is of great importance, since "over-decomposition" might partially "expunge" coefficients induced by the desired signal to be recovered, and "under-decomposition" might cause leakage of undesired wavelet coefficients into the estimate. Yet, practically, there is no problem to "capture" an optimal $L$.

For the reason of the space we omit demonstration of performance results of the above-described "estimation-by-projection" algorithm, which may be found in [14]. And now we would like to introduce the novel algorithm for the ultrasound pulse estimation based on the "de-noising" technique. Let us start this by a brief description of the de-noising method proposed by David L. Donoho and Iain M. Johnstone (1992).

6. DE-NOISING BY SOFT-THRESHOLDING

In 1992 David L. Donoho and Iain M. Johnstone have proposed a very simple thresholding procedure for recovering functions from noisy data. It consists of three steps defined as follows.

First step: Data signal (preferably consisting of $n = 2^J$ sample points, where $n, J \in Z$ ) is transformed into an orthogonal domain using periodized interval-adapted pyramidal algorithm of Cohen, Daubechies, Jawerth and Vial (1993), obtaining empirical wavelet coefficients.

Second step: The empirical wavelet coefficients are coordinatewise subjected to the soft-thresholding non-linearity $\eta_t(y) = sgh(y) \cdot (|y| - t)_+$ with specially chosen threshold $t_n = \sqrt{2 \cdot log(n)} \cdot \sigma$, where $\sigma$ is the standard deviation of the white noise.

Third step: The thresholded wavelet coefficients are inversely transformed into the original domain supplying us a noise-free estimation of the true signal.

We are far from to repeat all mathematical rigors of the experienced authors, which might be found in the original paper, but nevertheless, let us to point up several important features of the algorithm demonstrating its powerfulness and uniqueness.

We remind that the problem of the recovering of an unknown function from noisy data can be formulated as follows. Let $\{d_i\}_{i=0}^{n-1}$ denotes the noisy measurements of an unknown function $f(t)$ on $[0,1]$. Supposing the noise to be normal, independent identically distributed we have the following model $$d_i = f(t_i) + \sigma \cdot z_i, \quad i = 0,\ldots,n-1$$
$$\text{where } t_i = i/n \text{ and } z_i \stackrel{i.i.d}{\sim} N(0,1) \quad (4.1)$$

The goal is to optimize the mean-squared error $$\frac{1}{n} \cdot E\|\hat{f} - f\|_{l_n^2}^2 = \frac{1}{n} \cdot \sum_{i=0}^{n-1} E(\hat{f}(i/n) - f(i/n))^2. \quad (4.2)$$

It is important to emphasize that this minimization is subjected to the following additional side condition $$\text{with high probability}, \hat{f} \text{ is at least as smooth as } f \quad (4.3)$$

In order to implement this constrained minimization task the above-mentioned three-step algorithm was proposed. It was shown that this approach provides better quality than procedures based on mean-squared error alone.

It was completely proved that the proposed three-step algorithm has two unprecedented properties. First, with high probability the estimated signal is at least as smooth as the original one, with smoothness measured by any of a wide range of smoothness measures. Mathematically it is rephrased as the following. Let $S$ to be the scale of all spaces $B_{p,q}^{\sigma}$ (Besov classes) and all spaces $F_{p,q}^{\sigma}$ (Triebel classes) which embed continuously in $C[0,1]$, $\{\hat{f}_i^*(t_i)\}_{i=0}^{n-1}$ be the vector of estimated function values produced by the algorithm, and $\hat{f}_n^*(t)$ is a special smooth interpolation of these values producing a function on $[0,1]$. There are universal constants $(\pi_n)$ with $\pi_n \to 1$, $n = 2^{j_1} \to \infty$, and $C_1(F, \psi)$, which depends on the function space $F[0,1] \in S$ and on the wavelet basis, but not on $n$ or $f$, so that $$PROB\left\{\left\|\hat{f}_n^*\right\|_F \leq C_1 \cdot \|f\|_F, \quad \forall F \in S\right\} \geq \pi_n \qquad (4.4)$$

In words, $\hat{f}_n^*(t)$ is, with overwhelming probability, simultaneously as smooth as $f$ in every smoothness space $F$ taken from the scale S.

The second amazing property of the proposed algorithm is that the estimate achieves almost the *minimax error* over every one of a wide range of smoothness classes. Formally, let $F[0,1]$ be a function space (one of the Besov or Triebel spaces) and let $F_C$ denote the ball of functions $\{f : \|f\|_F \leq C\}$. Then the smallest error that can be achieved for any estimator, uniformly over all $f \in F_C$ is the *minimax mean-squared error* given by $$M(n, F_C) = \inf_{\hat{f}} \sup_{F_C} \frac{1}{n} \cdot E\left\|\hat{f}_n^* - f\right\|_{l_n^2}^2 \qquad (4.5)$$

For each ball $F_C$ arising from $F \in S$, there is a constant $C_2(F_C, \psi)$ which does not depend on $n$, such that for all $n = 2^{j_1}$, $j_1 > j_0$, $$\sup_{f \in F_C} E\left\|\hat{f}_n^* - f\right\|_{l_n^2}^2 \leq C_2 \cdot \log(n) \cdot \inf_{\hat{f}} \sup_{F_C} E\left\|\hat{f} - f\right\|_{l_n^2}^2 \qquad (4.6)$$

In words, $\hat{f}_n^*(t)$ is simultaneously within a logarithmic factor of *minimax* error over every Besov, Holder, Sobolev, and Triebel class contained in $C[0,1]$.

The properties are of great importance for understanding advantages of the proposed algorithm. The first one says that a recovered function with high probability is not contaminated by noise, i.e. the algorithm rejects the noise completely. The second one says that the estimate is nearly minimax over very wide range of smoothness classes. In general, existing non-wavelet methods can achieve the same success only over a limited range of the balls $F_c$ arising in the scale $S$ (basically $L^2$ Sobolev balls only), by relatively complicated means.

All above-mentioned advantages are really due to the Wavelet basis, and it was proved, that no analogous results could be achieved by using thresholding (or other possibly non-linear techniques) in the Fourier basis. The method works because the Wavelet transform of a noiseless (true) signal compresses its $l^2$ energy into a relative small number of large coefficients. On the other hand, Gaussian white noise in any one orthogonal basis is again a white noise in any other and with the same amplitude. Thus, in the orthogonal Wavelet basis, the "few" non-zero signal coefficients really stick up above the noise. Therefore, the thresholding of the wavelet coefficients has the effect that it kills the noise while not killing the signal.

Let's define the compression number $c_n$ (it measures how well a vector $f$ can be approximated by a vector with $n$ nonzero entries) as $$c_n \equiv \sum_{k>n} |f|^2_{(k)} \qquad (4.7)$$

Comparing of the extents to which the energy is compressed into a few big coefficients in the Fourier and Wavelet domains it may be demonstrated that in most practical cases for the same $n$ the magnitude of the $c_n$ in the Wavelet domain greater or equal to that in the Fourier domain. It guarantees that the ideal diagonal projector works better in the Wavelet basis than in the Fourier basis. The compression advantages of the Wavelet basis are responsible for the mean-squared error advantages of the thresholding of the wavelet coefficients.

Generally speaking the proposed de-noising algorithm is suited to work well, when a measured signal is contaminated by the white noise. Fortunately, it was showed that insignificant corrections are needed to adjust the algorithm to several other (not all)

noise types. Returning to our estimation problem we remind that the measured signal is the log-spectrum of a RF-line, and it is assumed combined from the desired signal to be estimated, i.e., the pulse log-spectrum, and noise, which is here the reflectivity function log-spectrum. A question that should be asked at this point is what's a kind of noise we have, and whether the de-noising algorithm is able to reject it? In order to answer this question we have to discuss statistical properties of the reflectivity function log-spectrum.

7. REFLECTIVITY LOG-SPECTRUM DISTRIBUTION

We assume that a chosen segment of RF-line obtained from a soft tissue is a coherent sum of echoes reflected from greatly large number of scatterers having randomly distributed reflection coefficients, and random, disordered locations. In such a case it is acceptable to think that according to the large numbers low, the scatterers distribution is close to be Gaussian, and consequently further we suppose that RF-line obtained from soft tissues is convolution of the ultrasound pulse with the white noise $\{a_i\}_{i=1}^{n} \sim N(0,\sigma^2)$. Let $\{\operatorname{Re} A_i\}_{i=1}^{n}$ denote the real part of the DFT of $\{a_i\}_{i=1}^{n}$ and $\{\operatorname{Im} A_i\}_{i=1}^{n}$ denote its imaginary part. Due to the orthogonality properties of the DFT $\{\operatorname{Re} A_i\}_{i=1}^{n}$ and $\{\operatorname{Im} A_i\}_{i=1}^{n}$ are uncorrelated and normally distributed.

$$\operatorname{Re} A = \frac{\{\operatorname{Re} A\}_{i=1}^{n}}{\sqrt{n/2}} \sim N(0, \sigma^2) \quad and \quad \operatorname{Im} A = \frac{\{\operatorname{Im} A\}_{i=1}^{n}}{\sqrt{n/2}} \sim N(0, \sigma^2) \qquad (5.1)$$

It can be shown that the probability distribution of $Z = \sqrt{\operatorname{Re} A^2 + \operatorname{Im} A^2}$ is the Rayleigh distribution whose probability density function is given as follows.

$$f_Z(z) = \frac{d}{dz} F(z) = \begin{cases} \frac{z}{\sigma^2} \exp\left(-\frac{z^2}{2\sigma^2}\right) & , z \geq 0 \\ 0 & , z < 0 \end{cases} \qquad (5.2)$$

According to (2.2) we compute the logarithm of $Z$ and we wish to investigate how this process affects its statistics. The density function of $Y = \log(Z)$ is given by $$f_Y(y) = \frac{f_Z(z)}{|dy/dz|} \qquad (5.3)$$

Using $\frac{dy}{dz} = \frac{1}{z} = \frac{1}{\exp(y)}$ we derive $$f_Y(y) = \frac{z^2}{\sigma^2} \cdot \exp\left(-\frac{z^2}{2\sigma^2}\right) = 2\frac{\exp(2y)}{2\sigma^2} \cdot \exp\left(-\frac{\exp(2y)}{2\sigma^2}\right) = \\ = 2 \cdot \exp\left(\left[2y - \ln(2\sigma^2)\right] - \exp\left(\left[2y - \ln(2\sigma^2)\right]\right)\right) \qquad (5.4)$$

The probability density function $f_Y(y)$ is of the Fisher-Tippet form (or doubly exponential form). When the second exponential is replaced by the first three terms of its serial expansion, we have $$f_Y(y) \cong \frac{2}{e} \cdot \exp\left(-\frac{[2y - \ln(2\sigma^2)]^2}{2}\right) = \frac{2}{e} \cdot \exp\left(-\frac{1}{2} \cdot \frac{\left[y - \frac{\ln(2\sigma^2)}{2}\right]^2}{0.25}\right) \qquad (5.5)$$

The significance of this expression is that the reflectivity function log-spectrum approximately can be viewed as a gaussian, random variable with the mean $\overline{Y} = \ln(2\sigma^2)/2$ and the *constant* variance $\sigma_Y^2 = 0.5^2$. It is quite amazing result saying that regardless the variance of the tissue reflectivity functions, its log-spectrum (i.e., logarithm of its DFT) is white noise with constant variance. From the viewpoint of the de-noising, we have a problem to cancel the white noise whose variance never changes. Note that the variance of the reflectivity functions does influence the mean of the distribution. Yet, it is unnecessary to try to compute and subtract it from RF-line log-spectrum, since its presence has no any destructive effect on the estimate quality (i.e., its only influence is multiplication of the estimate by a constant factor).

In Figure No3 (upper plot) one can see histograms (continuous lines) of simulated reflectivity function log-spectra built for different standard deviations of the reflectivity sequences, namely 0.5, 5, 40, and 200 (from left to right in the picture). The dotted lines denote the theoretically computed Fisher-Tippet probability density functions. One can see that, indeed, the mean values of the distributions depend on the reflectivity function variances ($\overline{Y} = \ln(2\sigma^2)/2$), whereas its variances remain approximately constant. Figure No3 (lower plot) shows the Fisher-Tippet distributions with its Gaussian approximations. One can see that in vicinity of the mean values the approximations are quite exact, whereas achieving the peripheries the approximation error becomes more significant. Nevertheless, very nearly we can accept this approximation as quite satisfactory.

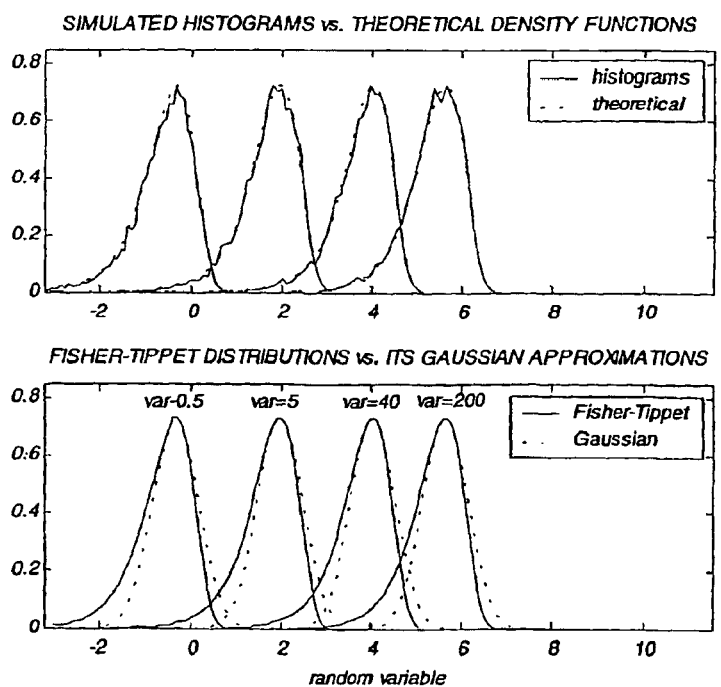

Figure No3: *(upper figure) simulated histograms via appropriate Fisher-Tippet probability density functions built for difference standard deviations of the reflectivity functions, namely 0.5, 5, 40, 200; (lower figure) above Fisher-Tippet probability density functions via its Gaussian approximations*

Table No1: *Comparison of first two moments of the Fisher-Tippet distribution and its Gaussian approximation computed for different values of the tissue reflectivity sequences*

| Reflectivity function standard deviation | Fisher-Tippet distribution | | Gaussian approximation | |
|---|---|---|---|---|
| | mean | variance | mean | variance |
| 0.5 | -0.62209 | 0.3736 | -0.34657 | 0.25 |
| 5 | 1.6676 | 0.41002 | 1.956 | 0.25 |
| 40 | 3.7469 | 0.4112 | 4.0355 | 0.25 |
| 200 | 5.3563 | 0.41123 | 5.6449 | 0.25 |

In the Table No1 the first two moments of the Fisher-Tippet distribution and its Gaussian approximation are compared. We see that independently of the reflectivity function variance the variance of the former is almost constant, that is in good agreement with the behavior of the Gaussian approximation variance.

Table No2: *Comparison of differences between first two moments of the Fisher-Tippet distribution and its Gaussian approximation computed for different values of the tissue reflectivity sequences*

| Reflectivity function standard deviation | Difference between the means of the Fisher-Tippet distribution and its Gaussian approximations (absolute values) | Difference between the variances of the Fisher-Tippet distribution and its Gaussian approximations | |
|---|---|---|---|
| | | absolute | relative (%) |
| 0.5 | 0.2755 | 0.1236 | 33.08 |
| 5 | 0.2884 | 0.1600 | 39.03 |
| 40 | 0.2886 | 0.1612 | 39.20 |
| 200 | 0.2886 | 0.1612 | 39.21 |

Table No2 shows the absolute and relative deference between the first two moments of the Fisher-Tippet distribution and its Gaussian approximation computed for different values of the reflectivity sequence variance. We note that the difference is almost constant, i.e. independently of the reflectivity function variance the mean of the approximation is shifted by a constant value relatively to the exact distribution mean, and likewise the ratio between the approximation variance and the real distribution variance is almost constant. From the above numerical results it stems that roughly we can take the value about 0.25 - 40%, as a *priori* guess about the "noise" variance.

It should be emphasized that the above Gaussian approximation is only an approximation, and frankly speaking there is a cardinal difference between these distributions. Attention should be drawn to the fact that the Fisher-Tippet distribution is non-symmetric. Let us highlight this point in more details.

In Figure No4 the Fisher-Tippet distribution is shown at once with its Gaussian approximation. Its right-hand side has a form nearly resembling the "Gaussian ball", but obviously having slightly smaller variance. One can observe that in this part the Gaussian distribution approximates quite satisfactory the exact one. In contrast the left-hand side of the Fisher-Tippet has a quite long "tail", giving rise to the variance larger than 0.25. Obviously, our approximation falls right here.

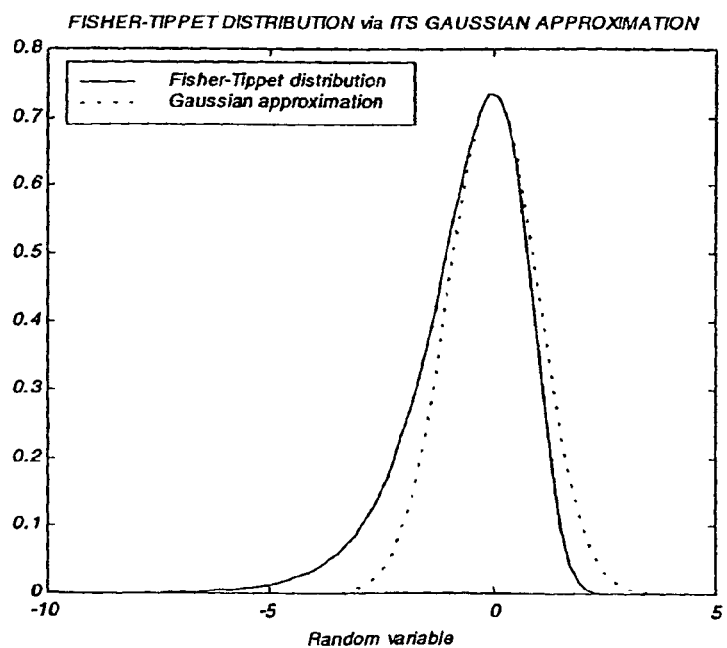

Figure No4: *The Fisher-Tippet distribution via its Gaussian approximation (appropriate to the reflectivity function standard deviation equal to 20)*

Figure No5 shows a typical Gaussian white noise sequence with unit variance (upper plot) and a typical Fisher-Tippet *i.i.d.* "noise" with variance $\sigma^2$ equal to 0.25 (lower plot). Note the straight lines determining regions of two standard deviations for both distributions. One can see that majority of the white noise samples (realizations) is concentrated in the region of $\pm 2\sigma$ and only its minor portion slightly extends beyond this region. In the same time the Fisher-Tippet behaves differently. Majority of its realizations is located within $\pm 2\sigma$ region resembling the white noise behavior, but there are also a few realizations, which are significantly "remote" from it (the left-hand "tail" of the Fisher-Tippet distribution is "responsible" for its appearance). Thus nearly this noise could be viewed as *white noise contaminated by occasional transients or "outliers"*. It was mentioned earlier that the three-step de-noising algorithm (as it was formulated initially) is more suitable for rejection of white, gaussian noises, inasmuch as it is based on a fundamental statistic consequence of the orthogonality of the DWT that transforms white noise into white noise of the same level. Thus it is reasonable to assume that the "outliers" might play a dramatic role here. There are two questions we have to ask. First, may we still use the originally proposed formula for the soft-threshold calculation, namely $t_n = \sqrt{2 \cdot \log(n)} \cdot \sigma$ (here $n$ is a number of data points and $\sigma$ is noise level)? Second, what is a better way to estimate the noise variance $\sigma^2$?

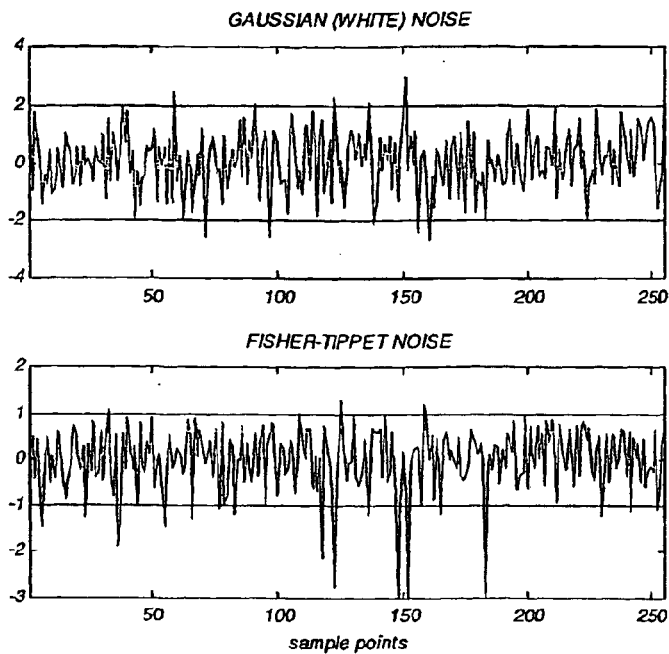

Figure No5: *(upper plot)* Gaussian (white) noise with $\sigma^2 = 1$; *(lower plot)* Fisher-Tippet noise with $\sigma^2 = 0.25$. The straight lines denote region of the two standard deviations.

In the previous chapter we have discussed the probability distribution of the "noise" to be rejected. Some conclusions were made on a behavior of the first two moments of its distribution. Nevertheless, in practice we often prefer to estimate it from data. Note that it does not contradict the above- obtained results, but we must note that it was obtained regardless possible measurement noises, and in order to turn the algorithm to be adaptive to possible "surprises", it make sense to estimate the moments. Usually, when a signal to be de-noised is band-limited and sampled by a frequency exceeding at least twice its Nyquist rate, the white noise variance can be estimated using wavelet coefficients of the finest decomposition level. Indeed, in such a case it is reasonable to assume that no induced-by-signal coefficients are present in this level, and only induced-by-noise coefficients are captured here. Using the fact that the white noise remains a white noise with the same level in the Wavelet domain, its variance can be estimated from these empirical wavelet coefficients. However, in number applications it could not be guaranteed that coefficients of the finest level do not contain the signal coefficients at all. Such situation is typical for number of the image processing applications, where edges usually induce wavelet coefficients in several levels including the finest. In order to obtain unbiased noise variance estimate based on the noise measurements in presence of few coefficients ascribed to the original signal, the following robust estimate is used. We can estimate the variance of the noise by assuming that *"most"* empirical wavelet coefficients in the finest of the decomposition are induced by the noise, and thus the *median absolute deviation* reflects the size of the typical noise. Dividing this value by 0.6745 we obtain a robust estimate of the noise standard deviation.

$$\sigma = MAD/0.6745,$$
$$\text{where } MAD = median(|wc - median(wc)|). \quad (6.1)$$

Here $n$ is the data length and $wc$ is the wavelet coefficient in the finest resolution levels.

Now let's return to our specific case and answer the question about a best strategy for the noise variance estimate. It has been argued previously that the pulse log-spectrum can be locally assimilated to a polynomial, thus it is reasonable to assume that the first (finest) decomposition level does not contain coefficients of the signal. Consequently, one can conclude that only coefficients we observe here are of the noise. At first glance, such a situation does not require using the robust median estimate according to (6.1), and we can compute it classically as $$\sigma = \sqrt{\frac{1}{n-1} \cdot \sum_{i=1}^{n} |wc - mean(wc)|^2} \quad (6.2)$$

Nevertheless, we prefer the median estimate for the following reason. The structure of the *i.i.d.* Fisher-Tippet noise is such that it can be approximately viewed as "contaminated-by-outliers white noise" (see above discussion about the Gaussian approximation of the Fisher-Tippet distribution, non-symmetry of the latter, and see Figure No5 for illustration). It is clear that these "transients" are captured in the *relatively large wavelet coefficients* of the finer resolution levels, whereas the other noise samples give rise to the wavelet coefficients distributed more or less with the same variance throughout all the levels. In such a case an estimate computed according to (6.2) from coefficients of the finest level consisting of the coefficients induced by the "gaussian" part of the Fisher-Tippet noise and bounded within the region of $\pm 2\sigma$, and few large "induced-by-outliers" coefficients, will be significantly biased by the latter. This estimate fairly reflects behavior of the second moment of the noise, but it might be greatly "dangerous" in the following sense. The greater the variance, the larger the threshold according to $t_n = \sqrt{2 \cdot \log(n)} \cdot \sigma$. Surely, that such a threshold guarantees suppression of the "induced-by-noise" coefficients, but also it might be too large and, consequently, it might suppress somewhat "induced-by-signal" wavelet coefficients causing oversmoothing of the result. In other words, few extreme, "from-the-distribution tail" noise samples might bias (enlarge) the variance estimate and, subsequently, the threshold value significantly, causing distortion (oversmoothing) of the de-noised signal. To avoid such situation, it makes sense to use (6.1) ignoring the "induced-by- transients" wavelet coefficients in the estimate. Of course in such a case, the threshold will kill most the noise coefficients, while allowing to the "induced- by-outliers" coefficients to pass into the signal estimate. In other words, these coefficients are viewed as being ascribed to the desired signal and having significant energy (due to the excellent compressing properties of the Wavelet transform) against a Gaussian white noise background. Subsequently, the thresholding procedure will keep it while expunging the "small" coefficients.

Obviously, such a mistake might be crucial, since the de-noised signal will have spurious, burst activity in finer resolution levels. Thus, the situation at hand is very contradictory. In order to prevent possible oversmoothing of the signal to be de-noised we have to set the threshold ignoring noise samples having extremely large variance, but from the other hand, it might give rise to the serious estimation error.

Figure No6 shows wavelet coefficients of the white noise with variance $\sigma^2 = 1$ (left-hand plot) and wavelet coefficients of the Fisher-Tippet noise with variance $\sigma^2 = 0.25$ (right-hand plot). Note that for both noises the dotted lines denotes the threshold computed according to (6.1) and $t_n = \sqrt{2 \cdot \log(n)} \cdot \sigma$. We see that *all* the white noise wavelet coefficients shown in the left-hand plot of the figure are "captured" by the threshold guaranteeing us a noise-free result. In the same time, the *most* (almost all) Fisher-Tippet noise coefficients are in the range to be shrunk, however there are few coefficients exceeding beyond the threshold. No doubts, that these coefficients can "spoil" all absolutely.

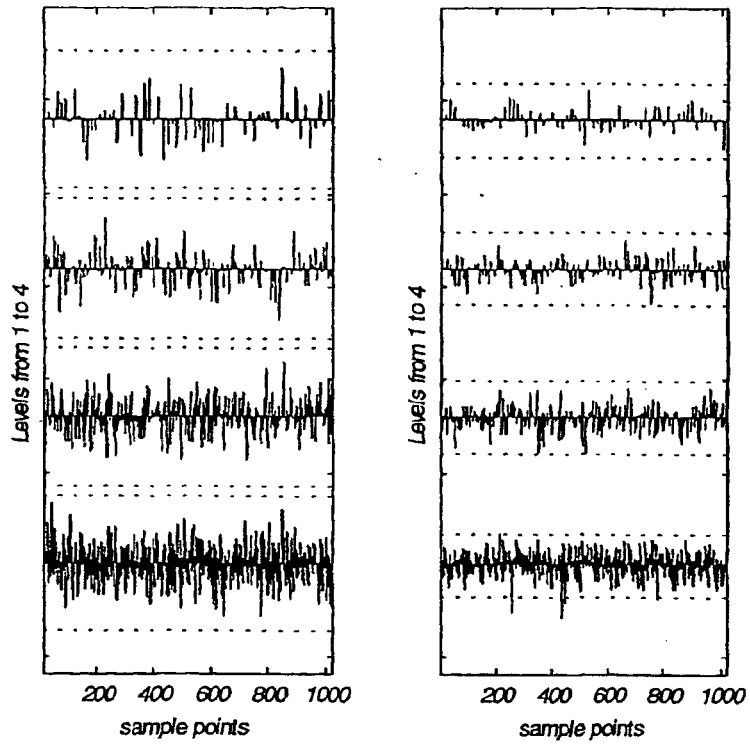

Figure No6: *(left-hand plot) wavelet coefficient of the white noise having unit variance, (right-hand plot) wavelet coefficients of the Fisher-Tippet noise with variance $\sigma^2 = 0.25$. Note that for both noises the dotted lines denotes the threshold computed according to (6.1) and $t_n = \sqrt{2 \cdot \log(n)} \cdot \sigma$.*

Whether the situation is hopeless? Not completely. In the next chapter we will suppose a very simple and efficient solution for it. Before this, we note that the same problem exists in the image processing applications considering the speckle noise reduction. It was shown (H. H. Arsenault, G. April, 1976 and D. L. Goodman, 1976), that the coherent speckle noise can be modeled as a multiplicative noise, i.e. an image contaminated by the speckle noise is the original image multiplied by the white Gaussian noise. Consequently, after the logarithmic transformation we have a sum of the logarithm of the origin to be recovered and the Fisher-Tippet ("almost Gaussian") noise. Thus the goal for speckle reduction is equivalent to finding the best estimate of the former by means of the wavelet shrinkage (i.e., non-linear thresholding of the wavelet coefficients), for instance, as it was reported in [11-12].

8. NON - LINEAR WAVELET ANALYSIS

The theory proposed by David Donoho and Iain Johnstone is based on the assumption that the noise contaminating a function to be recovered is close to the Gaussian, white noise. As a result, their three-step de-noising algorithm is very sensitive to outliers. In our specific case it falls for the noise samples coming from the "long tail" of the Fisher-Tippet distribution and having relatively large variance. The problem is that the "outliers" are treated as local features, and, consequently, preserved.

To take around this problem *Outlier resistant Wavelet transforms* was proposed in [13]. The pyramid algorithm was adapted to the form in which outliers are captured into robust residuals at different resolution levels. This algorithm was named *Smoother-Cleaner Wavelet Transform (SCWT)*. The idea is as follows. The DWT is a linear transformation, and consequently its coefficients are very sensitive to outliers. The classical Wavelet transform yields a sequence of approximations $f_k(t)$ of the original function $f(t)$. The approximations are nothing than the projections of the function into the sub- spaces spanned by the collection of scaling functions $$\phi_{k,m} = 2^{-\frac{k}{2}} \cdot \phi(2^{-k}t - m) \qquad (7.1)$$

In each sub-space each projection minimize the $L_2$ norm $$\| f(t) - f_k(t) \|_2^2 \qquad (7.2)$$

The problem is that the $L_2$ norm is extremely sensitive to outliers. At this point we have to note that it is very crucial to the projection method for estimation of the ultrasound pulse log-spectrum (see appropriate chapter). Let's remind that its estimate was obtained as a projection of the RF-line log-spectrum on an appropriate sub-space, i.e. the sub-space spanned by a collection the scaling functions (as it's given in (7.1)) with a prescribed index $k$. For the above- mentioned reason the outliers could significantly distort such an estimate. So the discussion below is also relevant to the projection algorithm.

One way to reduce the sensitivity of the Wavelet transform to outliers is to construct projections minimizing the $L_1$ norm (that is well known to be quite resistant to them). It was shown that in this case outliers could be captured completely in few projections onto complement sub-spaces, i.e. sub-spaces spanned by the collection of mother wavelets $$\psi_{k,m} = 2^{-\frac{k}{2}} \cdot \psi(2^{-k}t - m) \qquad (7.3)$$

In such a case it is easier to remove outliers from the $L_1$ decomposition. Unfortunately, this evidently attractive decomposition is inefficient from the computational point of view. For this reason SCWT was proposed. This Wavelet decomposition is very fast (computational complexity $O(n)$), and it performs like the classical Wavelet transform for Gaussian signals preventing outliers from leaking into the wavelet coefficients at coarser levels. The idea is to isolate wavelet coefficients probably ascribed to outliers in robust residuals at each resolution level.

Let's $S(k)$ denote wavelet coefficients at level $k$, and $\hat{S}(k)$ is a robust smooth of $S(k)$ obtained by running median of length 5 (note that the length of the robust filter should be as small as possible to provide minimal distortion of the underlying signal). The robust residuals $R(k)$ of the level $k$ are computed as follows $$R(k) = \begin{cases} 0, & \text{if } |S(k) - \hat{S}(k)| \leq \lambda_k \\ sign\left(S(k) - \hat{S}(k)\right) \cdot \left(|S(k) - \hat{S}(k)| - \lambda_k\right), & \text{if } |S(k) - \hat{S}(k)| \geq \lambda_k \end{cases} \qquad (7.4)$$

The threshold $\lambda_k$ is chosen so that most of the robust residuals are zeroed. Subsequently the classical Wavelet decomposition step resulting in detail and approximation wavelet coefficients $S(k+1)$ are applied to $[S(k) - R(k)]$. Clearly that the above steps are repeated with $S(k+1)$ and so on.

It was shown that in the Gaussian noise case, the proposed algorithm produce essentially the same decomposition as the classical DWT. When the signal to be analyzed is contaminated by a noise with outliers and its patches, it is completely captures in wavelet coefficients of finer levels retaining the signal approximation undistorted.

9. ESTIMATION BY ROBUST DE-NOISING

Returning to the pulse log-spectrum estimation problem, let's remind that it's equivalent to the problem of de-noising of the desired signal, when the noise to be rejected has the Fisher-Tippet distribution. In previous sections it was shown that a sequence of the noise could be viewed as a Gaussian white noise contaminated by "outliers" having extremely large variance. Generally, the residuals of the first decomposition level correspond to isolated outliers or pairs of outliers. In this case the simplest was to perform de-noising is to discard the robust residuals and to use wavelet shrinkage standard algorithm on the wavelet coefficients. The procedure is shown in the following block – diagram.

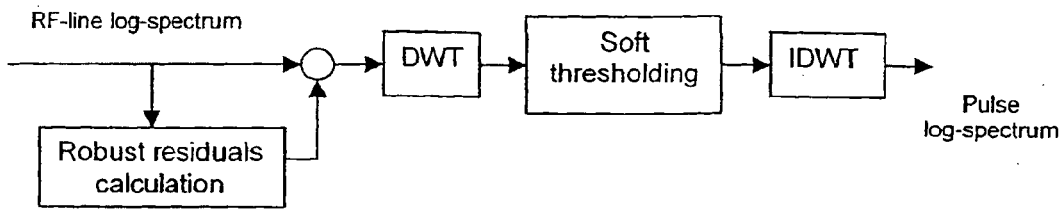

Block-diagram No1: *Robust ultrasound pulse log-spectrum estimation algorithm using outlier resistive de-noising*

In other words, in order to estimate the pulse log-spectrum we compute robust residual of a RF-line log-spectrum according to (7.4), then subtract it from the latter, and subsequently apply the classical de-noising algorithm of David L. Donoho and Iain Johnstone to the obtained difference.

Note that if the robust median filter is not long (from 5 to 7 points), then it has no any influence on the signal to be recovered. Consequently the above described subtraction and discard of residuals must change the probability distribution of the noise. This situation is depicted in Figure No7. In its upper plot one can see a histogram of a simulated $i.i.d.$ Fisher-Tippet sequence viewed at once with its theoretical Gaussian approximation. In the lower plot of the picture one can see the noise histogram after removing residuals, which were computed according to (7.4). Note the disappearance of the "long tail" indicating that all the "outliers" were removed. Additionally one can note that after the above "outlier shrinkage" procedure the noise distribution apparently resembles the Gaussian probability density function with variance that is very close to be theoretically predicted variance of the Gaussian approximation of the Fisher-Tippet distribution, namely 0.25. It guarantees that the "modified" noise does not include samples, which could be treaded as features of the signal to be recovered, and it is reasonable to expect that the three-step de- noising algorithm will supply us desired results.

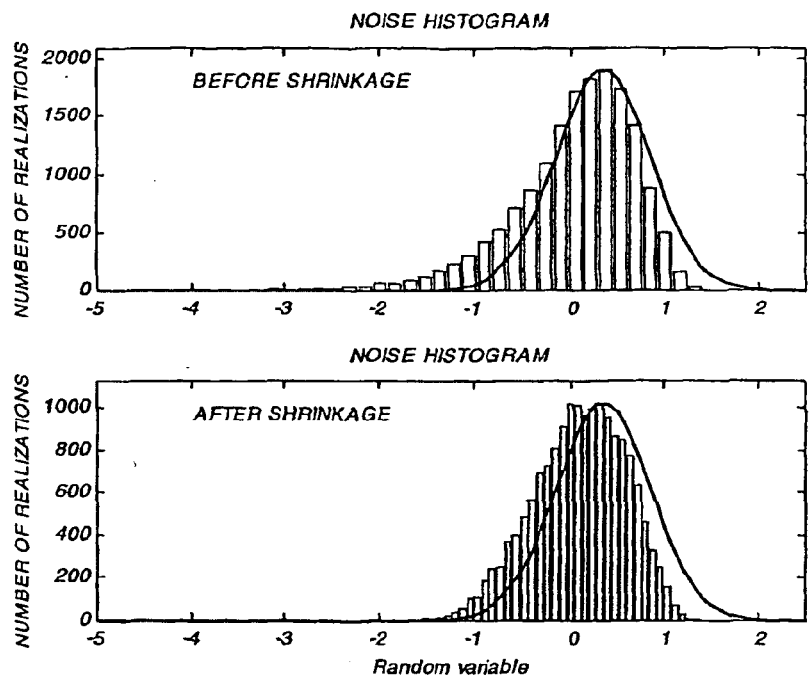

Figure No7: *(upper plot) simulated histogram the Fisher-Tippet "noise" via its theoretical Gaussian approximation, (lower plot) histogram of the above noise after removing its "outliers", samples having extremely large variance*

Before the demonstration of results we would like to add some notes regarding choice of the threshold in (7.4) and wavelet. In principal, we can compute the threshold value using theoretical value of the variance of the Gaussian approximation. Yet, from the practical point of view it was observed that one could obtain quite acceptable results choosing the threshold in such a way that 90-95% of the differences $[S(k) - \hat{S}(k)]$ are under it, and as a result are annihilated. Regarding the DWT filter choice it was observer that nearly symmetric filters of I. Daubechies perform very well.

Now let's show results of our computer simulations. In Figure No8 the necessity of using the smoothing-shrinkage step turning the reconstruction to be insensitive to "large-variance" samples of the Fisher- Tippet noise is demonstrated. The left-hand plot shoes the estimated pulse log-spectrum, when the estimation was performed using the classical three-step de-noising algorithm applied to the RF-line log-spectrum. One can see that indeed the noise "outliers" are treated as local features of the signal to be recovered, and consequently preserved in the reconstruction in the form of spurious details in finer resolution levels. In the right-hand plot one can see the same reconstruction preceded by the outliers smoothing-shrinkage step. Obviously there are no evident signs of influence the outliers on the estimate quality. From the quantitative point of view, the normalized mean-squared error in the first case is 4.736 %, whereas in the second case 3.982 %. Thus, one can conclude that the de-noising technique is a powerful tool for the pulse spectrum estimation, when it is preceded by the appropriate treatment of the noise "large-variance" samples.

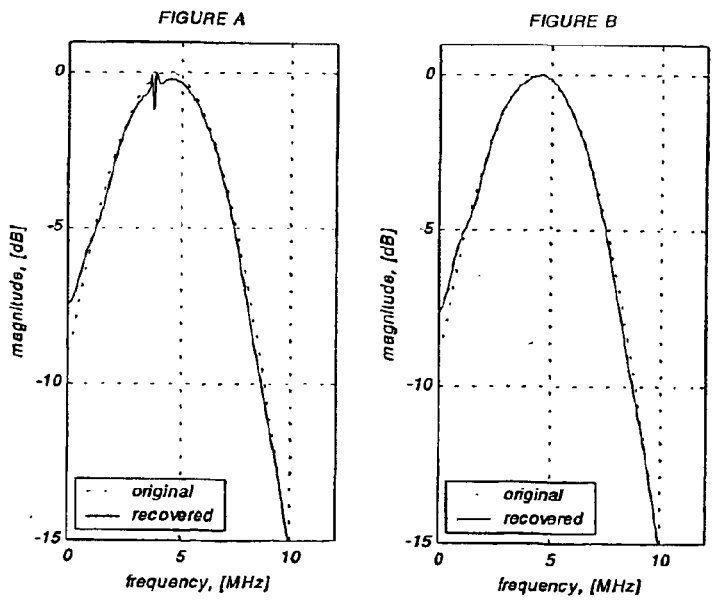

Figure No8: *(Figure A) estimated pulse log-spectrum (solid line) via original (dotted line). The estimated spectrum was obtained by de-noising RF-line log- spectrum without smoothing-shrinkage step. (Figure B) estimated pulse log-spectrum (solid*

*line) via original (dotted line). The estimated spectrum was obtained by de-noising RF-line log- spectrum with preceding smoothing- shrinkage procedure (see Block-diagram1).*

The proposed algorithm uses the decomposition of RF-line log-spectra in the dyadic Wavelet basis. However, it should be noted that the performance of the pulse estimation algorithm might be significantly improved by using another kinds of transformations, like Wavelet Packet, Trigonometric bases, Shift-Invariant libraries and etc., i.e., as it was described in [1-4]. So, many interesting questions remained out of scope of the paper. What results would be obtained by applying the technique in the "best" basis domain? Whether Translation-Invariant De-Noising can improve the pulse reconstruction quality? ... The work is not completed and the problem deserves further study.

10. REFERENCES

[1] "De-noising by Soft-Thresholding", David L. Donoho, 1992

[2] "Adapting to Unknown Smoothness via Wavelet Shrinkage "David L. Donoho and Iain Johnstone, 1993

[3] "Ideal De-noising in an Orthonormal Basis Chosen from a Library of Bases", David L. Donoho and Iain Johnstone, 1994

[4] "Translation-Invariant De-noising", David L. Donoho and R. R. Coifman, 1995

[5] "Wavelet shrinkage and Wavelet Vaguelette Decomposition: A Ten-Minute Tour", David L. Donoho, 1993

[6] "Nonlinear Wavelet Methods for Recovering Signals, Images, and Densities from indirect and noisy data", David L. Donoho, 1993

[7] "Wavelets on the intervals and fast wavelet transforms", A. Cohen, I. Daubechies, P. Vial, 1993

[8] "Properties of speckle integrated with a finite aperture and logarithmically transformed", H. H. Arsenault, G. April, Journal of Optical Society of America, 66, November, 1976

[9] "Some fundamental properties of speckle", D. L. Goodman, Journal of Optical Society of America, 66, November, 1976

[10] "Nonlinear processing of a shift invariant DWT for noise reduction", M. Lang, H. Guo, J. E. Odegard, and C. S. Burrus, SPIE, Vol. 2491, 1995

[11] "Simultaneous speckle reduction and data compression using best wavelet packet bases with application to SAR based ATD/R", D. Wei, J. E. Odegard, M. Lang, and C. S. Burrus, SPIE, Vol. 2491, 1995

[12] "Speckle reduction via Wavelet Shrinkage with application to SAR based ATD/R", H. Guo, J. E. Odegard, M. Lang, R. A. Gopinath, I. W. Selesnick, and C. S. Burrus, SPIE, Vol. 2303, 1994

[13] "De-noising and robust non-linear Wavelet analysis", Andrew G. Bruce, David L. Donoho, Hong-Ye Gao, R. Douglas Martin, SPIE, Vol. 2242, 1994

[14] "Nonparametric estimation of ultrasonic pulses using the FWT and determination of the reflectivity distribution using the approximate inverse technique", D. Adam, O. Michailovich, 2000, to be appeared.

What is claimed is:

1. A method of imaging a target, comprising the steps of:
   (a) acquiring an echo sequence image of the target;
   (b) computing a log spectrum of at least a portion of said echo sequence image;
   (c) computing a low-resolution wavelet projection of said log spectrum;
   (d) estimating a point spread function from said low-resolution wavelet projection; and
   (e) deconvolving said at least portion of said echo sequence image with said point spread function.

2. The method of claim 1, further comprising the step of:
   (f) partitioning the echo sequence image into a plurality of segments; said computing of said log spectrum, said computing of said wavelet projection, said estimating and said deconvolving then being effected separately for each said segment.

3. The method of claim 2, wherein said segments are disjoint.

4. The method of claim 2, wherein at least two of said segments at least partly overlap.

5. The method of claim 1, wherein said wavelet projection is based on a wavelet selected from the group consisting of Coiflet wavelets, minimum-phase Daubechies wavelets, symmetric Daubechies wavelets and biorthogonal wavelets.

6. The method of claim 1, wherein said computing of said wavelet projection includes effecting an outlier-resistant wavelet transform of said log spectrum.

7. The method of claim 1, wherein said estimating of said point spread function includes estimating a frequency domain phase of said point spread function.

8. The method of claim 7, wherein said phase estimating assumes that said point spread function is a minimum phase sequence.

9. The method of claim 1, wherein said deconvolving is effected using an approximate inverse.

10. A method of imaging a target, comprising the steps of:
    (a) acquiring an echo sequence image of the target;
    (b) computing a log spectrum of at least a portion of said echo sequence image;
    (c) effecting an outlier-resistant wavelet transform of said log spectrum, thereby producing a plurality of wavelet coefficients;
    (d) soft-thresholding said wavelet coefficients;
    (e) applying an inverse wavelet transform to said soft-thresholded wavelet coefficients to obtain a point spread function log spectrum;
    (f) estimating a point spread function from said point spread function log spectrum; and
    (g) deconvolving said at least portion of said echo sequence image with said point spread function.

11. The method of claim 10, further comprising the step of:
    (h) partitioning the echo sequence image into a plurality of segments; said computing of said log spectrum, said effecting of said wavelet transform, said soft-thresholding, said applying, said estimating and said deconvolving then being effected separately for each said segment.

12. The method of claim 11, wherein said segments are disjoint.

13. The method of claim 11, wherein at least two of said segments at least partly overlap.

14. The method of claim 10, wherein said outlier-resistant wavelet transform is based on minimizing an $L_1$ norm.

15. The method of claim 10, wherein said outlier-resistant wavelet transform is a Smoother-Cleaner Wavelet Transform.

16. The method of claim 10, wherein said outlier-resistant wavelet transform includes a plurality of resolution levels, with robust residuals being removed in only a portion of said resolution levels.

17. The method of claim 16, wherein said robust residuals are removed only in a first said resolution level.

18. The method of claim 10, wherein said estimating of said point spread function includes estimating a frequency domain phase of said point spread function.

19. The method of claim 18, wherein said phase estimating assumes that said point spread function is a minimum phase sequence.

20. The method of claim 10, wherein said deconvolving is effected using an approximate inverse.

21. An apparatus for imaging a target, comprising:
    (a) a transducer for acquiring an echo sequence image of the target; and
    (b) a processor for:
        (i) computing a log spectrum of at least a portion of said echo sequence image,
        (ii) computing a low-resolution wavelet projection of said log spectrum,
        (iii) estimating a point spread function from said low-resolution wavelet projection, and
        (iv) deconvolving said at least portion of said echo sequence image with said point spread function.

22. An apparatus for imaging a target, comprising:
    (a) a transducer for acquiring an echo sequence image of the target; and
    (b) a processor for:
        (i) computing a log spectrum of at least a portion of said echo sequence image,
        (ii) effecting an outlier-resistant wavelet transform of said at least portion of said log spectrum, thereby producing a plurality of wavelet coefficients,
        (iii) soft-thresholding said wavelet coefficients,
        (iv) applying an inverse wavelet transform to said soft-thresholded wavelet coefficients to obtain a point spread function log spectrum,
        (v) estimating a point spread function from said point spread function log spectrum, and
        (vi) deconvolving said at least portion of said echo sequence image with said point spread function.

* * * * *